(12) United States Patent
Kehler et al.

(10) Patent No.: US 7,678,800 B2
(45) Date of Patent: Mar. 16, 2010

(54) 2-(1H-INDOLYLSULFANYL)-ARYL AMINE DERIVATIVES FOR USE IN THE TREATMENT OF AFFECTIVE DISORDERS, PAIN, ADHD AND STRESS URINARY INCONTINENCE

(75) Inventors: Jan Kehler, Lyngby (DK); Friedrich Kroll, Mechelen (BE); Karsten Juhl, Greve (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 433 days.

(21) Appl. No.: 11/629,043

(22) PCT Filed: Jul. 13, 2005

(86) PCT No.: PCT/DK2005/000491

§ 371 (c)(1),
(2), (4) Date: Aug. 31, 2007

(87) PCT Pub. No.: WO2006/007843

PCT Pub. Date: Jan. 26, 2006

(65) Prior Publication Data

US 2008/0027074 A1    Jan. 31, 2008

(30) Foreign Application Priority Data

Jul. 16, 2004  (DK) .................. 2004 01121
Jun. 17, 2005  (DK) .................. 2005 00893

(51) Int. Cl.
*A61K 31/496* (2006.01)
*A61K 31/454* (2006.01)
*A61K 31/4439* (2006.01)
*C07D 209/30* (2006.01)
*C07D 401/121* (2006.01)

(52) U.S. Cl. .......... 514/254.09; 514/323; 514/339; 544/373; 546/201; 546/277.7

(58) Field of Classification Search ........... None
See application file for complete search history.

(56) References Cited

U.S. PATENT DOCUMENTS

| | | | |
|---|---|---|---|
| 3,803,143 A | 4/1974 | Tanaka et al. | |
| 4,018,830 A | 4/1977 | Christy et al. | |
| 4,055,665 A | 10/1977 | Christy et al. | |
| 4,056,632 A | 11/1977 | Mehta et al. | |
| 4,198,417 A | 4/1980 | Ong et al. | |
| 4,241,071 A | 12/1980 | Martin et al. | |
| 5,095,039 A | 3/1992 | Mehta et al. | |
| 5,945,425 A | 8/1999 | Moormann et al. | |
| 6,410,736 B1 | 6/2002 | Howard et al. | |
| 6,436,938 B1 | 8/2002 | Howard et al. | |
| 6,455,738 B1 | 9/2002 | Dubac et al. | |
| 6,509,340 B1 | 1/2003 | Van Amsterdam et al. | |
| 6,596,741 B2 | 7/2003 | Howard et al. | |
| 6,906,078 B2 | 6/2005 | Moorman et al. | |
| 7,189,501 B2 | 3/2007 | Makuta et al. | |
| 7,199,147 B2 | 4/2007 | Imazaki et al. | |
| 7,217,732 B2 | 5/2007 | Kozlowski et al. | |
| 7,229,751 B2 | 6/2007 | Kimura et al. | |
| 7,247,651 B2 | 7/2007 | Madera et al. | |
| 2002/0173524 A1 | 11/2002 | Collins et al. | |
| 2003/0187023 A1 | 10/2003 | Kubo et al. | |
| 2003/0207894 A1 | 11/2003 | Theodoridis et al. | |
| 2004/0009959 A1 | 1/2004 | Potter et al. | |
| 2004/0014774 A1 | 1/2004 | Myers et al. | |
| 2004/0023010 A1 | 2/2004 | Bulovic et al. | |
| 2004/0039035 A1 | 2/2004 | Collins et al. | |
| 2004/0072844 A1 | 4/2004 | Madera et al. | |
| 2004/0077854 A1 | 4/2004 | Halazy et al. | |
| 2004/0132778 A1 | 7/2004 | Lacadie et al. | |
| 2004/0137389 A1 | 7/2004 | Fukui et al. | |
| 2004/0176426 A1 | 9/2004 | Houze et al. | |
| 2004/0186148 A1 | 9/2004 | Shankar et al. | |
| 2004/0192664 A1 | 9/2004 | Kunz et al. | |
| 2004/0204451 A1 | 10/2004 | Lacadie et al. | |
| 2004/0209936 A1 | 10/2004 | Bratton et al. | |
| 2004/0220237 A1 | 11/2004 | Fu et al. | |
| 2004/0266732 A1 | 12/2004 | Galvez et al. | |

(Continued)

FOREIGN PATENT DOCUMENTS

EP    0 273 199 A2    7/1988

(Continued)

OTHER PUBLICATIONS

Axford, L., et al. "Bicyclo[2.2.1]heptanes as Novel Triple Re-uptake inhibitors for the Treatment of Depression", Bioorganic & Medicinal Chemistry Letters, 2003, pp. 3277-3280, vol. 13.

(Continued)

*Primary Examiner*—Emily Bernhardt
(74) *Attorney, Agent, or Firm*—Stephen G. Kalinchak; Margaret M. Buck; Mary C. Johnson

(57) ABSTRACT

The present invention relates to 2-(1H-indolylsulfanyl)-aryl amine derivatives of the general formula I

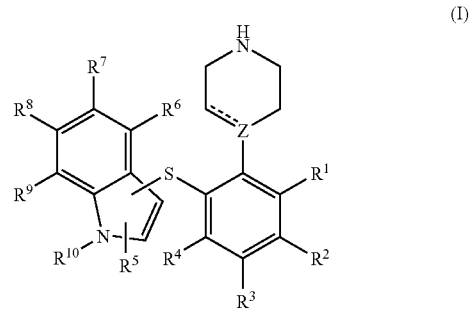

as the free base or salts thereof and their use for the treatment of affective disorders, pain, attention deficit hyperactivity disorder (ADHD) and stress urinary incontinence.

29 Claims, No Drawings

U.S. PATENT DOCUMENTS

| | | | |
|---|---|---|---|
| 2005/0107599 | A1 | 5/2005 | Makioka et al. |
| 2005/0123501 | A1 | 6/2005 | Lewis |
| 2005/0136065 | A1 | 6/2005 | Valiante, Jr. |
| 2005/0152859 | A1 | 7/2005 | Dooley et al. |
| 2005/0153980 | A1 | 7/2005 | Schadt, Jr. et al. |
| 2005/0159556 | A1 | 7/2005 | Lewis et al. |
| 2005/0189519 | A1 | 9/2005 | Gothe et al. |
| 2005/0206994 | A1 | 9/2005 | Kokeguchi et al. |
| 2005/0228020 | A1 | 10/2005 | Miyamoto et al. |
| 2005/0238992 | A1 | 10/2005 | Kodama |
| 2005/0250794 | A1 | 11/2005 | Napper et al. |
| 2005/0261298 | A1 | 11/2005 | Solow-Cordero et al. |
| 2005/0282861 | A1 | 12/2005 | Friary et al. |
| 2006/0030593 | A1 | 2/2006 | Bernotas et al. |
| 2006/0069203 | A1 | 3/2006 | Lewis et al. |
| 2007/0004923 | A1 | 1/2007 | Kobayashi et al. |
| 2007/0054904 | A1 | 3/2007 | Knolle et al. |
| 2007/0060595 | A1 | 3/2007 | Yoshizawa et al. |

FOREIGN PATENT DOCUMENTS

| | | | |
|---|---|---|---|
| EP | 0 396 827 A1 | | 11/1990 |
| EP | 0 402 097 A1 | | 12/1990 |
| EP | 0 755 923 A1 | | 1/1997 |
| EP | 0 814 084 A1 | | 12/1997 |
| EP | 0 921 124 A1 | | 6/1999 |
| WO | WO 93/11106 A1 | | 6/1993 |
| WO | WO 93/12080 | | 6/1993 |
| WO | WO 94/14770 A1 | | 7/1994 |
| WO | WO 97/17325 | | 5/1997 |
| WO | WO 97/17352 A1 | | 5/1997 |
| WO | WO 97/48698 A1 | | 12/1997 |
| WO | WO 98/08817 | | 3/1998 |
| WO | WO 00/59878 | | 10/2000 |
| WO | WO 00/66537 | | 11/2000 |
| WO | WO 01/10842 A2 | | 2/2001 |
| WO | WO 01/27068 A1 | | 4/2001 |
| WO | WO 01/49677 A1 | | 7/2001 |
| WO | WO 01/49678 A1 | | 7/2001 |
| WO | WO 01/49679 A1 | | 7/2001 |
| WO | WO 02/40024 A1 | | 5/2002 |
| WO | WO 02/062766 A2 | | 8/2002 |
| WO | WO 02/098857 A1 | | 12/2002 |
| WO | WO 03/029232 | | 4/2003 |
| WO | WO 03/055873 A1 | | 7/2003 |
| WO | 2004/035047 | * | 4/2004 |
| WO | WO 2005/061455 | | 7/2005 |
| WO | WO 2006/006172 A2 | | 1/2006 |
| WO | WO 2006/098380 A1 | | 9/2006 |

OTHER PUBLICATIONS

Edmond, P., et al. "Substituted Diphenyl Sulfides as Selective Serotonin Transporter Ligands: Synthesis and In Vitro Evaluation", J. Med. Chem., 2002, pp. 1253-1258, vol. 45.

Hawkins, D.G., et al. "Competitive Cyclisation of Singlet and Triplet Nitrenes. Part 7. Reaction Pathways of 2-Azidophenyl Benzothienyl Azides", Journal of the Chemical Society, Perkin Transactions I: Organic and Bio-Organic Chemistry, 1979, pp. 3207-3210, No. 12.

Jackson, A., et al. "Electrophilic Substitution in Indoles Part 16 1,2 The Formation of Indolobenzothiazines and Indolobenzothiazepines by Intramolecular Cyclisation of (o-Nitrophenylthio)indoles", J. Chem. Res. Miniprint, 1988, pp. 2017-2063, vol. 9.

Jilek, J., et al. "Potential Antidepressants: 2-(Methoxy- and Hydroxy-Phenylthio)Benzylamines as Selective Inhibitors of 5-Hydroxytryptamine Re-Uptake in the Brain", Collect. Czech. Chem. Commun., 1989, pp. 3294-3338, vol. 54.

Martin, L., et al. "Synthesis of Spiro[isobenzofuran-1(3H),4'-piperidines] as Potential Central Nervous System Agents. 5. Conformationally Mobile Analogues Derived by Furan Ring Opening", J. Med. Chem., 1979, pp. 1347-1354, vol. 22, No. 11.

Oya, S., et al. "A New Single-Photon Emission Computed Tomography Imaging Agent for Serotonin Transporters: [123I] IDAM, 5-Iodo-2-((2-((dimethylamino)methyl)-phenyl)thio)benzyl Alcohol", J. Med. Chem., 1999, pp. 333-335, vol. 42 (3).

Oya, S., et al. "New PET Imaging Agent for the Serotonin Transporter: [18F]ACF (2-[(2-Amino-4-chloro-5-fluorophenyl)thio]-N,N-dimethyl-benzenmethanamine)", J. Med. Chem., 2002, pp. 4716-4723, vol. 45.

Ragno, R., et al., "Docking and 3-D QSAR Studies on Indolyl Aryl Sulfones. Binding Mode Exploration at the HIV-1 Reverse Transcriptase Non-Nucleoside Binding Site and Design of Highly Active N-(2-Hydroxyethyl)carboxamide and N-(2-Hydroxyethyl)carbohydrazide Derivatives", J. Med. Chem., 2005, pp. 213-223, vol. 48.

Silvestri, R., et al., "Novel Indolyl Aryl Sulfones Active against HIV-1 Carrying NNRTI Resistance Mutations: Synthesis and SAR Studies", J. Med. Chemistry, 2003, pp. 2482-2493, vol. 46.

Sindelar, K., et al. "Potential Antidepressants and Inhibitors of 5-Hydroxy-Tryptamine and Noradrenaline Re-Uptake in the Brain: N,N-Dimethyl-(Arylthio)Thenylamines and N,N-Dimethyl-2-(Thienylthio) Benzylamines", Collect. Czech. Chem. Commun., 1991, pp. 449-458, vol. 56.

Wong, D.T. "Duloxetine (LY 248686): an inhibitor of Serotonin and noradrenaline uptake and antidepressant drug candidate" Exp. Opin. Invest. Drugs, 1998, 7(10), 1691-1699.

Khan, et al. "Venlafaxine in Depressed Outpatients" Psychopharmacology Bulletin, 1991, 27, 141-144.

Katzman, M. "Venlafaxine in the Treatment of Anxiety Disorders" Expert Rev. Neurotherapeutics, 2004, 4(3), 371-381.

NME Drug and New Biologic Approvals in 2004 [online] retrieved on Jun. 4, 2009; retrieved from the Internet [URL; http://www.fda.gov/Drugs/DevelopmentApprovalProcess/HowDrugsareDevelopedandApproved/DrugandBiologicApprovalReports/NMEDrugandNewBiologicApprovals/ucm081677.htm].

May 20, 2008 NDA Approval Letter [online] retrieved on Jun. 4, 2009; retrieved from the Internet [URL; http://www.accessdata.fda.gov/drugsatfda_docs/appletter/2008/022104s000ltr.pdf].

Berk, M. "Duloxetine: A review" Expert Rev. Neurotherapeutics, 2003, 3 (4), 447-451.

Fishbain, et al. "Evidence-Based Data From Animal and Human Experimental Studies on Pain Relief with Anti-depressants: A Structural Review" Pain Medicine, 2000, 1(4), 310-316.

CDER New Molecular Entity (NME) Drug and New Biologic Approvals for Calendar Year 2009 (Updated through Apr. 30, 2009) [online] retrieved on Jun. 4, 2009; retrieved from the Internet [URL; http://www.fda.gov/downloads/Drugs/DevelopmentApprovalProcess/HowDrugsareDevelopedandApproved/DrugandBiologicApprovalReports/NMEDrugandNewBiologicApprovals/UCM091096.pdf].

Mukaddes, et al. "Venlafaxine in Attention Deficit Hyperactivity Disorder" European Neurophyschopharmacology, 2002, 12, supplement 3, p. 421.

Dmochowski, et al. "Duloxetine Versus Placebo for the Treatment of North American Women with Stress Urinary Incontinence" The Journal of Urology, 2003, 170, 1259-1263.

Depressed Mood [online] retrieved on Dec. 2, 2008; retrieved from the Internet [URL; http://www.healthline.com/adamcontent/depresion].

Fibromyalgia [online] retrieved on Dec. 2, 2008; retrieved from the Internet [URL; http://www.nlm.nih.gov/medlineplus/ency/article/000427.htm].

Obsessive-compulsive disorder [online] retrieved on Dec. 2, 2008; retrieved from the Internet [URL; http://www.nlm.nih.gov/medlineplus/ency/article/000929.htm].

Abstract and STN Search Report cited in the Jul. 10, 2008 Office Action in connection with parallel U.S. Appl. No. 11/452,823.

A. Burger, "Isosterism and Bioisosterism in drug design". Prog. Drug Res. 1991, 37:287-371.

Mitra, et al.; "Thiophenes & Thiapyrans: Part XVII—Thieno-(2:3-b)-thionaphthene & Thionaphtheno-(2:3-b)-thionaphthene". Journal of Scientific & Industrial Research., 1957, 16B:348-54.

Sejberg, J. Synth[e]sis of 3- and 2-phenylsulfanyl-1H-indole [thesis] (English Translation). Lyngby (Denmark): Technical University of Denmark: Jan. 21, 2003. 102 pages (Tables 6,7 and 8 are attached at the end of the document). Available from: Technical University of Denmark, Lyngby, DK; d991811.

* cited by examiner

2-(1H-INDOLYLSULFANYL)-ARYL AMINE DERIVATIVES FOR USE IN THE TREATMENT OF AFFECTIVE DISORDERS, PAIN, ADHD AND STRESS URINARY INCONTINENCE

This application is a §371(a) national stage of PCT International Application No. PCT/DK2005/000491, filed Jul. 13, 2005 on behalf of H. Lundbeck A/S, and claims the benefit of priority under 35 U.S.C. §119(e) of U.S. Provisional Application No. 60/588,555, filed Jul. 16, 2004 and of U.S. Provisional Application No. 60/691,736, filed Jun. 17, 2005; and claims the benefit of priority under 35 U.S.C. §119(a)-(d) of Danish Application No. PA200401121, filed Jul. 16, 2004, and of Danish Application No. PA200500893, filed Jun. 17, 2005, the contents of all the preceding applications are hereby incorporated by reference into the subject application.

FIELD OF THE INVENTION

The present invention relates to compounds, which are serotonin reuptake inhibitors and preferably also norepinephrine reuptake inhibitors and/or dopamine reuptake inhibitors and the medical use of such compounds, e.g., in the treatment of affective disorders, pain disorders, attention deficit hyperactivity disorder (ADHD) and stress urinary incontinence.

BACKGROUND OF THE INVENTION

All currently available antidepressants can be classified in 3 classes:
1) monoamine oxidase inhibitors (MAOIs),
2) biogenic amine neurotransmitter [serotonin (5-HT), norepinephrine (NE) and dopamine (DA)] transporter reuptake blockers, and
3) modulators, especially blockers of one or more of the 5-HT and/or NE receptors.

Since depression is associated with a relative deficiency of the biogenic amines, the use of 5-HT and/or NE-receptor blockers (i.e. 5-HT and or NE-antagonist's) have not proven very successful in the treatment of depression and anxiety and the preferred and currently most efficient treatments are based on the enhancement of 5-HT and/or NE neurotransmission by blocking their reuptake back from the synaptic cleft (Slattery, D. A. et al., "The evolution of antidepressant mechanisms", *fundamental and Clinical pharmacology,* 2004, 18, 1-21; Schloss, P. et al, "new insights into the mechanism of antidepressant therapy", *Pharmacology and therapeutics,* 2004, 102, 47-60).

Selective serotonin reuptake inhibitors (hereinafter referred to as SSRIs) have become first choice therapeutics in the treatment of depression, certain forms of anxiety and social phobias, because they generally are effective, well tolerated and have a favourable safety profile compared to the classic tricyclic antidepressants. Drugs claimed to be SSRIs are for example fluoxetine, sertraline and paroxetine.

However, clinical studies on depression indicate that non-response to the known SSRIs is substantial, up to 30%. Another, often neglected, factor in antidepressant treatment is the fact that there is generally a delay in therapeutic effect of the SSRIs. Sometimes symptoms even worsen during the first weeks of treatment. Furthermore, sexual dysfunction is generally a side effect common to SSRIs. Accordingly, there is a desire for the development of compounds capable of improving the treatment of depression and other serotonin related diseases.

A newer strategy has been the development of dual re-uptake inhibitors, e.g., the combined effect of 5-HT reuptake inhibition and NE (norepinephrine is also named noradrenaline, NA) reuptake-inhibition on depression is explored in clinical studies of compounds such as Duloxetine (Wong, "Duloxetine (LY-248686): an inhibitor of serotonin and noradrenaline uptake and an antidepressant drug candidate", *Expert Opinion on Investigational Drugs,* 1998, 7, 10, 1691-1699) and Venlafaxine (Khan-A et al, 30 "Venlafaxine in depressed outpatients", *Psychopharmacology Bulletin,* 1991, 27, 141-144). Compounds having such dual effect are also named SNRIs, "serotonin and noradrenaline reuptake inhibitors", or NSRIs, "noradrenaline and serotonin reuptake inhibitors".

Since treatment with the selective NE reuptake inhibitor reboxetine has been shown to stimulate 5-HT neurons and mediate the release of 5-HT in the brain (Svensson, T. et al, *J. Neural. Transmission,* 2004, 111, 127) there might be a synergistic advantage using SNRI's in the treatment of depression or anxiety.

The use of SNRI's have been shown in clinical studies to have a beneficial effect on pain (e.g. Fibromyalgia syndrome, overall pain, back pain, shoulder pain, headache, pain while awake and during daily activities) and especially pain associated with depression (Berk, M. *Expert Rev. Neurotherapeutics* 2003, 3, 47-451; Fishbain, D. A., et al. "Evidence-based data from animal and human experimental studies on pain relief with antidepressants: A structured review" Pain Medicine 2000 1:310-316).

SNRI's have also been shown in clinical studies to have a beneficial effect in attention deficit hyperactivity disorder (ADHD) (N. M. Mukaddes; Venlafaxine in attention deficit hyperactivity disorder, European Neuropsychopharmacology, Volume 12, Supplement 3, October 2002, Page 421).

Furthermore, SNRI's have been shown to be effective for the treatment of stress urinary incontinence (Dmochowski R. R. et al. "Duloxetine versus placebo for the treatment of North American women with stress urinary incontinence", Journal of Urology 2003, 170:4, 1259-1263.)

Naranjo, C. et al. "The role of the brain reward system in depression" *Prog. Neuro-Psychopharmacol. Biol. Psychiatry* 2001, 25, 781-823 discloses clinical and preclinical findings of links between lack of extra cellular dopamine in the mesocorticolimbic system and anhedonia, which is one of the main symptoms of depression.

Furthermore, Axford L. et al. describe the development of triple 5-HT, NE and DA re-uptake inhibitors for treatment of depression. (2003, *Bioorganic & Medical Chemistry Letters,* 13, 3277-3280: "Bicyclo[2.2.1.]heptanes as novel triple re-uptake inhibitors for the treatment of depression"). Wellbutrin (bupropion) which has DA re-uptake activity in vitro and in vivo, show antidepressant efficacy. Other combination studies have indicated that addition of some affinity at the DA uptake site may have some clinical benefit (Nelson, J. C. *J. Clin. Psychiatry* 1998, 59, 65; Masand, P. S. et al. *Depression Anxiety* 1998, 7, 89; Bodkin, J. A et al. *J. Clin. Psychiatry* 1997, 58, 137).

The combination of an SSRI and a norepinephrine and dopamine reuptake inhibitor, has been shown to have better efficacy in SSRI-non-responders (Lam R. W. et al. "Citalopram and Bupropion-SR: Combining Versus Switching in Patients With Treatment-Resistant Depression." *J. Clin. Psychiatry* 2004, 65, 337-340).

There is clinical evidence suggesting that the combination of an SSRI and a norepinephrine and dopamine reuptake inhibitor induces less sexual dysfunction, than treatment with SSRI's alone (Kennedy S. H. et al. "Combining Bupropion SR With Venlafaxine, Paroxetine, or Duloxetine: A Preliminary Report on Pharmacokinetic, Therapeutic, and Sexual Dysfunction Effects" *J. Clin. Psychiatry* 2002, 63, 181-186).

Diphenyl sulphides of Formula II and variations thereof have been disclosed as serotonin re-uptake inhibitors and have been suggested for use in treatment of depression, cf. e.g. WO03029232(A1).

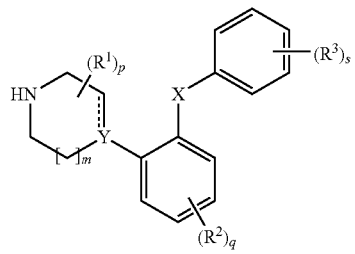

The above-mentioned reference does not disclose compounds comprising an indole group like the indolyl-sulfanyl arylamines of the present invention.

Diphenyl sulphides of Formula (IIA) and variations thereof have been disclosed as serotonin re-uptake inhibitors and have been suggested for use in treatment of depression, cf. e.g. U.S. Pat. No. 5,095,039, U.S. Pat. No. 4,056,632, EP 396827 A1 and WO 9312080. EP 402097 describes halogen substituted diphenylsulfides claimed to be selective serotonin inhibitors for treatment of depression. Likewise WO 9717325 disclose derivatives of N,N-dimethyl-2-(arylthio)benzylamine claimed to be selective serotonin transport inhibitors and suggest their use as antidepressants. J. Jilek et al., 1989, Collect. Czeck Chem. Commun., 54, 3294-3338 also discloses various derivatives of diphenyl sulphides, "phenylthio-benzylamines" as antidepressants. Furthermore, diphenyl sulphides are also disclosed in U.S. Pat. No. 3,803,143 and claimed useful as antidepressant.

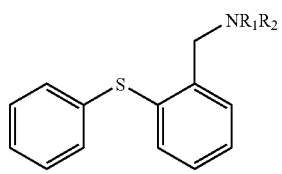

K. Sindelar et al., "Collection of Czechoslovak Chemical Communications, (1991), 56(2), 449-58, by K. Sindelar et al" disclose compounds of Formula (IIB) in which one of the rings is substituted with a thiophene ring with test for selectivity as 5-HT re-uptake inhibitor and NA re-uptake inhibitor, respectively, for use as antidepressants.

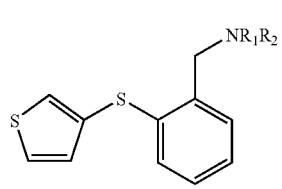

The present invention provides 2-(1H-indolylsulfanyl)-aryl amine derivatives of formula I which are serotonin reuptake inhibitors. A particular aspect of the invention provides compounds possessing the combined effect of serotonin reuptake inhibition and norepinephrine reuptake inhibition. Another particular aspect of the invention provides compounds possessing the combined effect of serotonin reuptake inhibition and dopamine reuptake inhibition. Furthermore, some of the compounds are also triple 5-HT, NE and DA re-uptake inhibitors.

SUMMARY OF THE INVENTION

One object of the invention is the provision of compounds, which are serotonin reuptake inhibitors. Another object of the invention is the provision of compounds, which are both serotonin reuptake inhibitors and noradrenaline reuptake inhibitors. Yet another object of the invention is the provision of compounds, which are both serotonin reuptake inhibitors and dopamine reuptake inhibitors. Yet another object of the invention is the provision of compounds, which are serotonin reuptake inhibitors, noradrenaline reuptake inhibitors and dopamine reuptake inhibitors.

The compounds of the invention are substituted indole derivatives of the general formula I as the free base or salts thereof

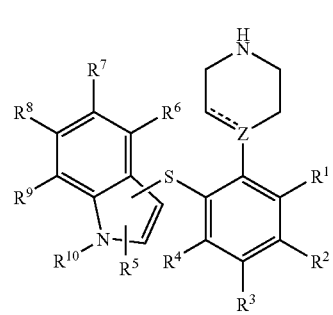

wherein Z, the dotted line and $R^1$-$R^{10}$ are as defined below.

The invention provides a compound according to the above for use as a medicament.

The invention provides a pharmaceutical composition comprising a compound according to the above and at least one pharmaceutically acceptable carrier or diluent.

The invention provides the use of a compound according to the above for the preparation of a-medicament for the treatment of affective disorders, pain disorders, ADHD and stress urinary incontinence.

The invention furthermore concerns the use of a compound according to the above in a method of treatment of affective disorders, pain disorders, ADHD and stress urinary incontinence.

DEFINITION OF SUBSTITUENTS

The term heteroatom refers to a nitrogen, oxygen or sulphur atom.

Halo means halogen. Halogen means fluoro, chloro, bromo or iodo.

The expression "$C_{1-6}$-alk(en/yn)yl" means a $C_{1-6}$-alkyl, a $C_{2-6}$-alkenyl or a $C_{2-6}$-alkynyl group. The expression "$C_{1-6}$-alk(en)yl" means a $C_{1-6}$-alkyl or a $C_{2-6}$-alkenyl group. The term "$C_{1-6}$-alkyl" refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl.

The term "$C_{2-6}$-alkenyl" designates such groups having from two to six carbon atoms, including one double bond, including but not limited to ethenyl, propenyl, and butenyl. Such $C_{2-6}$-alkenyl group may be branched or unbranched.

The term "$C_{2-6}$-alkynyl" designates such groups having from two to six carbon atoms, including one triple bond, including but not limited to ethynyl, propynyl and butynyl. Such $C_{2-6}$-alkynyl group may be branched or unbranched.

The expression "$C_{3-8}$-cycloalk(en)yl" means a $C_{3-8}$-cycloalkyl or a $C_{3-8}$-cycloalkenyl group. The term "$C_{3-8}$-cycloalkyl" designates a monocyclic or bicyclic carbocycle having three to eight C-atoms, including but not limited to cyclopropyl, cyclopentyl, and cyclohexyl. The term "$C_{3-8}$-cycloalkenyl" designates a monocyclic or bicyclic carbocycle having three to eight C-atoms and one double bond, including but not limited to cyclopropenyl, cyclopentenyl and cyclohexenyl.

In the expression "$C_{3-8}$-cycloalk(en)yl-$C_{1-6}$-alk(en/yn)yl", "$C_{1-6}$-alk(en/yn)ylamino", "di-($C_{1-6}$-alk(en/yn)yl)amino", "$C_{1-6}$-alk(en/yn)ylcarbonyl", "$C_{1-6}$-alk(en/yn)ylaminocarbonyl", "di-($C_{1-6}$-alk(en)yl)aminocarbonyl", "$C_{1-6}$-alk(en/yn)yloxy", "$C_{1-6}$-alk(en/yn)ylsulfanyl", "halo-$C_{1-6}$-alk(en/yn)yl", "halo-$C_{1-6}$-alk(en/yn)ylsulfonyl", "halo-$C_{1-6}$-alk(en/yn)ylsulfanyl", "$C_{1-6}$-alk(en/yn)yl-O—CO—" and "$C_{1-6}$-alk(en/yn)ylsulfonyl" the terms "$C_{3-8}$-cycloalk(en)yl", "$C_{1-6}$-alk(en/yn)yl", "$C_{1-6}$-alk(en)yl" and "halo" are as defined above.

DESCRIPTION OF THE INVENTION

The present invention relates to 2-(1H-indolylsulfanyl)-aryl amine-derivatives which are serotonin reuptake inhibitors, some of the compounds are also noradrenaline reuptake inhibitors. Furthermore, some compounds of the invention are serotonin reuptake inhibitors and dopamine reuptake inhibitors. Furthermore, some compounds of the invention are serotonin reuptake inhibitors, noradrenaline reuptake inhibitors and dopamine reuptake inhibitors. Accordingly, the compounds of the invention are considered to be useful in the treatment of affective disorders such as for example depression and anxiety.

The present invention relates to a compound represented by the general formula I as the free base or salts thereof

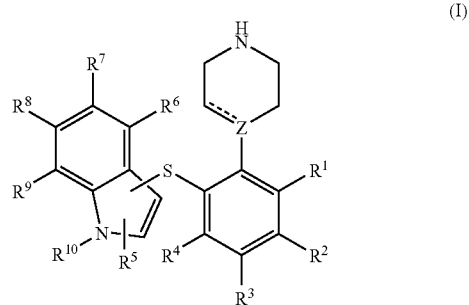

(I)

wherein the dotted line represents an optional bond;

and each of $R^1$-$R^4$ is independently selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl; and $R^5$ is selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl; and each of $R^6$-$R^9$ is independently selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl, $C_{1-6}$-alk(en/yn)ylsulfonyl and $C_{1-6}$-alk(en/yn)yl-O—CO—;

and $R^{10}$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

and

Z is selected from the group consisting of N, CH and C, with the proviso that the dotted line represents a bond when Z is C and with the proviso that the dotted line does not represent a bond when Z is N or CH.

In one embodiment of the compound of formula I, the dotted line ---- represents a bond. In another embodiment of the compound of formula I the dotted line ---- does not represent a bond.

In a further embodiment of the compound of formula I, the dotted line ---- does not represent a bond and Z represents a nitrogen atom. In a further embodiment of the compound of formula I, the dotted line ---- does not represent a bond and Z represents CH. In a further embodiment of the compound of formula I, the dotted line ---- represents a bond and Z represents a carbon atom.

In a further embodiment of the compound of formula I each of $R^{1-4}$ is independently selected from the group consisting of nitro, amino, $C_{1-6}$-alk(en/yn)ylamino, di-($C_{1-6}$-alk(en/yn)yl) amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl; in another embodiment each of $R^{1-4}$ is independently selected from the group consisting of hydrogen, halogen, cyano, $C_{1-6}$-alk(en/yn)yl, $C_{3-8}$-cycloalk(en)yl and $C_{3-8}$-cycloalk(en)yl-$C_{1-6}$-alk(en/yn)yl. Typically, each of $R^{1-4}$ is independently selected from the group consisting of hydrogen, halogen and $C_{1-6}$-alk(en/yn)yl. To further illustrate without limiting the invention, an embodiment concerns such compounds wherein at least one of $R^{1-4}$ is hydrogen; in a further embodiment at least one of $R^{1-4}$ is halogen such as fluoro; in a further embodiment at least one of $R^{1-4}$ is $C_{1-6}$-alk(en/yn)yl such as methyl.

In a further embodiment of the compound of formula I, $R^1$ is hydrogen.

In a further embodiment of the compound of formula I, $R^1$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl. Typically, $R^2$ is selected from the group consisting of hydrogen and $C_{1-6}$-alk(en/yn)yl. To further illustrate without limiting the invention an embodiment of $R^2$ is hydrogen; another embodiment of $R^2$ is $C_{1-6}$-alk(en/yn)yl typically $C_{1-6}$-alkyl such as methyl.

In a further embodiment of the compound of formula I, $R^3$ is hydrogen.

In a further embodiment of the compound of formula I, $R^4$ is selected from the group consisting of hydrogen, halogen and cyano. Typically, $R^4$ is selected from the group consisting of hydrogen and halogen. To further illustrate without limiting the invention an embodiment of $R^4$ is hydrogen; another embodiment of $R^4$ is halogen such as fluoro.

In a further embodiment of the compound of formula I $R^5$ is selected from the group consisting of halogen, cyano, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl; in another embodiment $R^5$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl. Typically, $R^5$ is selected from the group consisting of hydrogen and $C_{1-6}$-alk(en/yn)yl. To further illustrate without limiting the invention an embodiment of $R^5$ is hydrogen; another embodiment of $R^5$ is $C_{1-6}$-alk(en/yn)yl typically $C_{1-6}$-alkyl such as methyl.

In a further embodiment of the compound of formula I, $R^5$ is attached to position 2 of the indole moiety. In a further embodiment of the compound of formula I, $R^5$ is attached to position 3 of the indole moiety.

In a further embodiment of the compound of formula I each of $R^{6-9}$ is independently selected from the group consisting of amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl; in another embodiment each of $R^{6-9}$ is independently selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yloxy and $C_{1-6}$-alk(en/yn)yl-O—CO—. Typically, each of $R^{6-9}$ is independently selected from the group consisting of hydrogen, halogen, nitro, $C_{1-6}$-alk(en/yn)yl, $C_{1-6}$-alk(en/yn)yloxy and $C_{1-6}$-alk(en/yn)yl-O—CO—. To further illustrate without limiting the invention, an embodiment concerns such compounds wherein at least one of $R^{6-9}$ is hydrogen; in a further embodiment at least one of $R^{6-9}$ is halogen such as chloro or fluoro; in a further embodiment at least one of $R^{6-9}$ is nitro; in a further embodiment at least one of $R^{6-9}$ is $C_{1-6}$-alk(en/yn)yl typically $C_{1-6}$-alkyl such as methyl or ethyl; in a further embodiment at least one of $R^{6-9}$ is $C_{1-6}$-alk(en/yn)yloxy typically $C_{1-6}$-alkyloxy such as methoxy; in a further embodiment at least one of $R^{6-9}$ is $C_{1-6}$-alk(en/yn)yl-O—CO— typically $C_{1-6}$-alkyl-O—CO— such as $CH_3$—O—CO—.

In a further embodiment of the compound of formula I, $R^6$ is selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl and $C_{1-6}$-alk(en/yn)yloxy. Typically, $R^6$ is selected from the group consisting of hydrogen, halogen, $C_{1-6}$-alk(en/yn)yl, $C_{1-6}$-alk(en/yn)yloxy. To further illustrate without limiting the invention an embodiment of $R^6$ is hydrogen, another embodiment of $R^6$ is halogen such as chloro or fluoro; another embodiment of $R^6$ is $C_{1-6}$-alk(en/yn)yl typically $C_{1-6}$-alkyl such as methyl; another embodiment of $R^6$ is $C_{1-6}$-alk(en/yn)yloxy typically $C_{1-6}$-alkyloxy such as methoxy.

In a further embodiment of the compound of formula I, $R^7$ is selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yloxy and $C_{1-6}$-alk(en/yn)yl-O—CO—. Typically, $R^7$ is selected from the group consisting of hydrogen, halogen, nitro, $C_{1-6}$-alk(en/yn)yl, $C_{1-6}$-alk(en/yn)yloxy and $C_{1-6}$-alk(en/yn)yl-O—CO—. To further illustrate without limiting the invention an embodiment of $R^7$ is hydrogen, another embodiment of $R^7$ is halogen such as chloro or fluoro; another embodiment of $R^7$ is nitro; another embodiment of $R^7$ is $C_{1-6}$-alk(en/yn)yl typically $C_{1-6}$-alkyl such as methyl, another embodiment of $R^7$ is $C_{1-6}$-alk(en/yn)yloxy typically $C_{1-6}$-alkyloxy such as methoxy; another embodiment of $R^7$ is $C_{1-6}$-alk(en/yn)yl-O—CO— typically $C_{1-6}$-alkyl-O—CO— such as Me-O—CO—.

In a further embodiment of the compound of formula I, $R^8$ is selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl and $C_{1-6}$-alk(en/yn)yloxy. Typically, $R^8$ is selected from the group consisting of hydrogen, halogen, $C_{1-6}$-alk(en/yn)yl and $C_{1-6}$-alk(en/yn)yloxy. To further illustrate without limiting the invention an embodiment of $R^8$ is hydrogen; another embodiment of $R^8$ is halogen such as chloro or fluoro; another embodiment of $R^8$ is $C_{1-6}$-alk(en/yn)yl typically $C_{1-6}$-alkyl such as methyl; another embodiment of $R^8$ is $C_{1-6}$-alk(en/yn)yloxy typically $C_{1-6}$-alkyloxy such as methoxy.

In a further embodiment of the compound of formula I, $R^9$ is selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yloxy and $C_{1-6}$-alk(en/yn)yl-O—CO—. Typically, $R^9$ is selected from the group consisting of hydrogen, halogen, $C_{1-6}$-alk(en/yn)yl, $C_{1-6}$-alk(en/yn)yloxy, $C_{1-6}$-alk(en/yn)yl-O—CO—. To further illustrate without limiting the invention an embodiment of $R^9$ is hydrogen; another embodiment of $R^9$ is halogen such as chloro or fluoro; another embodiment of $R^9$ is $C_{1-6}$-alk(en/yn)yl typically $C_{1-6}$-alkyl such as methyl or ethyl; another embodiment of $R^9$ is $C_{1-6}$-alk(en/yn)yloxy typically $C_{1-6}$-alkyloxy such as methoxy; another embodiment of $R^9$ is $C_{1-6}$-alk(en/yn)yl-O—CO— typically $C_{1-6}$-alkyl-O—CO— such as Me-O—CO—.

In a further embodiment of the compound of formula I $R^{10}$ is selected from the group consisting of hydrogen and $C_{1-6}$-alk(en/yn)yl. To further illustrate without limiting the invention an embodiment of $R^{10}$ is hydrogen; another embodiment of $R^{10}$ is $C_{1-6}$-alk(en/yn)yl typically $C_{1-6}$-alkyl such as methyl.

To further illustrate without limiting the invention independent embodiments concerns such compounds wherein halogen typically is fluoro or chloro.

$C_{1-6}$-alk(en/yn)yl typically is $C_{1-6}$-alkyl, such as methyl.

$C_{3-8}$-cycloalk(en)yl typically is $C_{3-8}$-cycloalkyl.

$C_{3-8}$-cycloalk(en)yl-$C_{1-6}$-alk(en/yn)yl typically is $C_{3-8}$-cycloalkyl-$C_{1-6}$-alkyl.

$C_{1-6}$-alk(en/yn)ylamino typically is $C_{1-6}$-alkylamino.

di-($C_{1-6}$-alk(en/yn)yl)amino typically is di-($C_{1-6}$-alkyl)amino.

$C_{1-6}$-alk(en/yn)ylcarbonyl typically is $C_{1-6}$-alkylcarbonyl.

$C_{1-6}$-alk(en/yn)ylaminocarbonyl typically is $C_{1-6}$-alkylaminocarbonyl.

di-($C_{1-6}$-alk(en)yl)aminocarbonyl typically is di-($C_{1-6}$-alkyl)aminocarbonyl.

$C_{1-6}$-alk(en/yn)yloxy typically is $C_{1-6}$-alkoxy, such as methoxy.

$C_{1-6}$-alk(en/yn)ylsulfanyl typically is $C_{1-6}$-alkylsulfanyl, such as methylsulfanyl.

halo-$C_{1-6}$-alk(en/yn)yl typically is halo-$C_{1-6}$-alkyl, such as trifluoromethyl.

halo-$C_{1-6}$-alk(en/yn)ylsulfonyl typically is trifluoromethylsulfonyl.

halo-$C_{1-6}$-alk(en/yn)ylsulfanyl typically is trifluoromethylsulfanyl $C_{1-6}$-alk(en/yn)ylsulfonyl typically is $C_{1-6}$-alkylsulfonyl.

In a further embodiment, the invention concerns such compounds wherein 0, 1, 2 or 3 of $R^{1-10}$ are different from hydrogen, typically 1 or 2 of $R^{1-10}$ are different from hydrogen. In a further embodiment 0 or 1 of $R^{1-4}$ is different from hydrogen and 0, 1 or 2 of $R^{6-9}$ is/are different from hydrogen. In a further embodiment, none of $R^{1-10}$ is different from hydrogen. In a further embodiment, one of $R^{1-10}$ is different from hydrogen. A further embodiment concerns such compounds wherein one of $R^{1-4}$ is different from hydrogen and none of $R^{6-10}$ is hydrogen; in a further embodiment one of $R^{6-10}$ is different from hydrogen and none of $R^{1-4}$ is hydrogen. In a further embodiment two of $R^{1-10}$ are different from hydrogen. To further illustrate without limiting the invention an embodiment concerns such compounds wherein zero of $R^{1-4}$ are different from hydrogen and two of $R^{6-9}$ are different from hydrogen; in another embodiment one of $R^{1-4}$ is different from hydrogen and one of $R^{6-9}$ is different from hydrogen. In a further embodiment three of $R^{1-10}$ are different from hydrogen. To further illustrate without limiting the invention an embodiment concerns such compounds wherein one of $R^{1-4}$ is different from hydrogen and two of $R^{6-9}$ are different from hydrogen. In each embodiment, as mentioned the remaining substituents are hydrogen.

To further illustrate without limiting the invention, an embodiment concerns such compounds wherein $R^1$ is different from hydrogen;

another embodiment concerns such compounds wherein $R^2$ is different from hydrogen;

another embodiment concerns such compounds wherein $R^3$ is different from hydrogen;

another embodiment concerns such compounds wherein $R^4$ is different from hydrogen;

another embodiment concerns such compounds wherein $R^5$ is different from hydrogen;

another embodiment concerns such compounds wherein $R^6$ is different from hydrogen;

another embodiment concerns such compounds wherein $R^7$ is different from hydrogen;

another embodiment concerns such compounds wherein $R^8$ is different from hydrogen;

another embodiment concerns such compounds wherein $R^9$ is different from hydrogen;

another embodiment concerns such compounds wherein $R^{10}$ is different from hydrogen.

In a further embodiment of the compound of formula I, $R^5$ is attached to position 2 of the indole. Such compounds are embraced by the below formula IA:

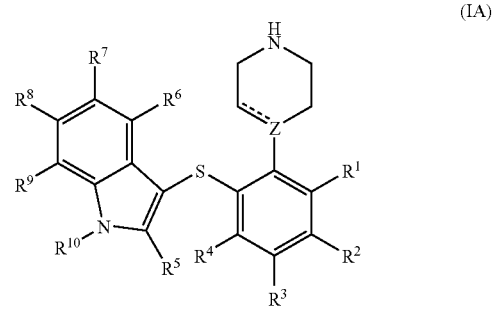

(IA)

wherein Z, the dotted line and $R^1$-$R^{10}$ are as defined under formula I. Any one of the embodiments related to formula I is also an embodiment of formula IA.

In a further embodiment of the compound of formula I, $R^5$ is attached to position 3 of the indole. Such compounds are embraced by the below formula IB:

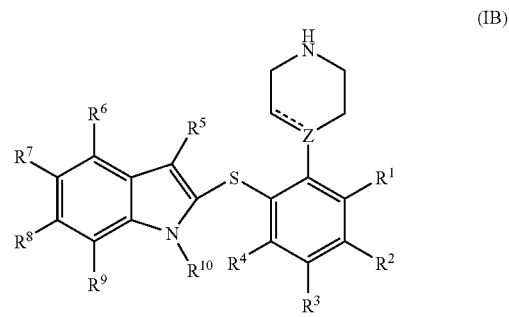

(IB)

wherein Z, the dotted line and $R^1$-$R^{10}$ are as defined under formula I. Any one of the embodiments related to formula I is also an embodiment of formula IB.

In a further embodiment of the compound of formula IB, each of $R^{1-4}$ is independently selected from the group consisting of hydrogen and $C_{1-6}$-alk(en/yn)yl.

In a further embodiment of the compound of formula IB, $R^5$ is $C_{1-6}$-alk(en/yn)yl In a further embodiment of the compound of formula IB, each of $R^{6-9}$ are hydrogen.

In a further embodiment of the compound of formula IB, $R^{10}$ is hydrogen.

In a further embodiment of the compound of formula I the dotted line does not represent a line and Z is N. Such compounds are embraced by the below formula IC:

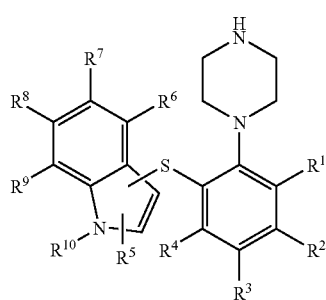

(IC)

wherein $R^1$-$R^{10}$ are as defined under formula I. Any one of the embodiments related to formula I is also an embodiment of formula IC.

In a further embodiment of the compound of formula IC, each of $R^{1-4}$ is independently selected from the group consisting of hydrogen, halogen and $C_{1-6}$-alk(en/yn)yl. Typically, $R^1$ is hydrogen; $R^2$ is hydrogen or $C_{1-6}$-alk(en/yn)yl; $R^3$ is hydrogen and $R^4$ is hydrogen or halogen.

In a further embodiment of the compound of formula IC, $R^5$ is hydrogen or $C_{1-6}$-alk(en/yn)yl.

In a further embodiment of the compound of formula IC, each of $R^{6-9}$ is independently selected from the group consisting of hydrogen, halogen, $C_{1-6}$-alk(en/yn)yl, $C_{1-6}$-alk(en/yn)yloxy, $C_{1-6}$-alk(en/yn)yl-O—CO— and $NO_2$. Typically, $R^6$ is hydrogen, halogen, $C_{1-6}$-alk(en/yn)yl or $C_{1-6}$-alk(en/yn)yloxy; $R^7$ is hydrogen, halogen, $C_{1-6}$-alk(en/yn)yl, $C_{1-6}$-alk(en/yn)yloxy or $NO_2$; $R^8$ is hydrogen, halogen, $C_{1-6}$-alk(en/yn)yl or $C_{1-6}$-alk(en/yn)yloxy; and $R^9$ is hydrogen, halogen, $C_{1-6}$-alk(en/yn)yl, $C_{1-6}$-alk(en/yn)yloxy or $C_{1-6}$-alk(en/yn)yl-O—CO—.

In a further embodiment of the compound of formula IC, $R^{10}$ is hydrogen or $C_{1-6}$-alk(en/yn)yl.

In a further embodiment of the compound of formula I the dotted line represents a line and Z is C. Such compounds are embraced by the below formula ID:

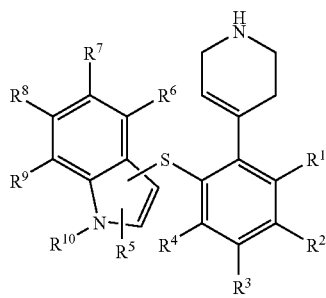

(ID)

wherein $R^1$-$R^{10}$ are as defined under formula I. Any one of the embodiments related to formula I is also an embodiment of formula ID.

In a further embodiment of the compound of formula ID, each of $R^{1-10}$ are hydrogen atoms In a further embodiment of the compound of formula I the dotted line does not represent a line and Z is CH. Such compounds are embraced by the below formula IE:

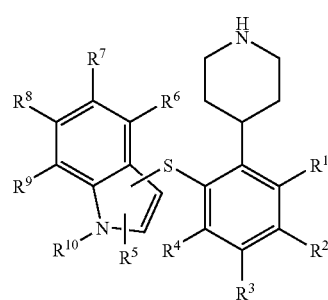

(IE)

wherein $R^1$-$R^{10}$ are as defined under formula I. Any one of the embodiments related to formula I is also an embodiment of formula IE.

In a further embodiment of the compound of formula IE, each of $R^{1-4}$ are hydrogen.

In a further embodiment of the compound of formula IE, $R^5$ is hydrogen or $C_{1-6}$-alk(en/yn)yl.

In a further embodiment of the compound of formula IE, each of $R^{6-9}$ is hydrogen, halogen, $C_{1-6}$-alk(en/yn)yl or $C_{1-6}$-alk(en/yn)yloxy. Typically, $R^6$ is hydrogen, halogen or $C_{1-6}$-alk(en/yn)yl; $R^7$ is hydrogen, halogen, $C_{1-6}$-alk(en/yn)yl or $C_{1-6}$-alk(en/yn)yloxy; $R^8$ is hydrogen or halogen; $R^9$ is hydrogen, halogen, $C_{1-6}$-alk(en/yn)yl or $C_{1-6}$-alk(en/yn)yloxy.

In a further embodiment of the compound of formula IE, $R^{10}$ is hydrogen or $C_{1-6}$-alk(en/yn)yl.

In a further embodiment of the compound of formula I said compound is selected from the following list of compounds

| Compound no. | Name |
|---|---|
| 1 | 3-(2-Piperazin-1-yl-phenylsulfanyl)-1H-indole |
| 2 | 4-Methoxy-3-(2-piperazin-1-yl-phenylsulfanyl)-1H-indole |
| 3 | 3-(2-Piperazin-1-yl-phenylsulfanyl)-1H-indole-7-carboxylic acid methyl ester |
| 4 | 5-Nitro-3-(2-piperazin-1-yl-phenylsulfanyl)-1H-indole |
| 5 | 6-Chloro-3-(2-piperazin-1-yl-phenylsulfanyl)-1H-indole |
| 6 | 6-Methoxy-3-(2-piperazin-1-yl-phenylsulfanyl)-1H-indole |
| 7 | 6-Fluoro-3-(2-piperazin-1-yl-phenylsulfanyl)-1H-indole |
| 8 | 7-Methyl-3-(2-piperazin-1-yl-phenylsulfanyl)-1H-indole |
| 9 | 3-[2-(1,2,3,6-Tetrahydro-pyridin-4-yl)-phenylsulfanyl]-1H-indole |
| 10 | 6-Methyl-3-(2-piperazin-1-yl-phenylsulfanyl)-1H-indole |
| 11 | 4-Fluoro-3-(2-piperazin-1-yl-phenylsulfanyl)-1H-indole |
| 12 | 5-Fluoro-3-(2-piperazin-1-yl-phenylsulfanyl)-1H-indole |
| 13 | 4-Methyl-3-(4-methyl-2-piperazin-1-yl-phenylsulfanyl)-1H-indole |
| 14 | 6-Fluoro-3-(4-methyl-2-piperazin-1-yl-phenylsulfanyl)-1H-indole |
| 15 | 4-Fluoro-3-(4-methyl-2-piperazin-1-yl-phenylsulfanyl)-1H-indole |
| 16 | 7-Fluoro-3-(4-methyl-2-piperazin-1-yl-phenylsulfanyl)-1H-indole |
| 17 | 5-Methoxy-4-methyl-3-(4-methyl-2-piperazin-1-yl-phenylsulfanyl)-1H-indole |
| 18 | 5-Methoxy-3-(4-methyl-2-piperazin-1-yl-phenylsulfanyl)-1H-indole |
| 19 | 7-Methoxy-3-(4-methyl-2-piperazin-1-yl-phenylsulfanyl)-1H-indole |
| 20 | 4-Methoxy-3-(4-methyl-2-piperazin-1-yl-phenylsulfanyl)-1H-indole |
| 21 | 4-Chloro-3-(4-methyl-2-piperazin-1-yl-phenylsulfanyl)-1H-indole |
| 22 | 7-Chloro-3-(4-methyl-2-piperazin-1-yl-phenylsulfanyl)-1H-indole |

-continued

| Compound no. | Name |
|---|---|
| 23 | 1-Methyl-3-(4-methyl-2-piperazin-1-yl-phenylsulfanyl)-1H-indole |
| 24 | 3-Methyl-2-(4-methyl-2-piperazin-1-yl-phenylsulfanyl)-1H-indole |
| 25 | 2-Methyl-3-(2-piperazin-1-yl-phenylsulfanyl)-1H-indole |
| 26 | 5-Methyl-3-(2-piperazin-1-yl-phenylsulfanyl)-1H-indole |
| 27 | 4-Methyl-3-(2-piperazin-1-yl-phenylsulfanyl)-1H-indole |
| 28 | 7-Fluoro-3-(2-piperazin-1-yl-phenylsulfanyl)-1H-indole |
| 29 | 7-Ethyl-3-(2-piperazin-1-yl-phenylsulfanyl)-1H-indole |
| 30 | 5-Methoxy-4-methyl-3-(2-piperazin-1-yl-phenylsulfanyl)-1H-indole |
| 31 | 5-Methoxy-3-(2-piperazin-1-yl-phenylsulfanyl)-1H-indole |
| 32 | 7-Methoxy-3-(2-piperazin-1-yl-phenylsulfanyl)-1H-indole |
| 33 | 5-Fluoro-2-methyl-3-(2-piperazin-1-yl-phenylsulfanyl)-1H-indole |
| 34 | 5-Chloro-3-(2-piperazin-1-yl-phenylsulfanyl)-1H-indole |
| 35 | 4-Chloro-3-(2-piperazin-1-yl-phenylsulfanyl)-1H-indole |
| 36 | 7-Chloro-3-(2-piperazin-1-yl-phenylsulfanyl)-1H-indole |
| 37 | 1-Methyl-3-(2-piperazin-1-yl-phenylsulfanyl)-1H-indole |
| 38 | 3-Methyl-2-(2-piperazin-1-yl-phenylsulfanyl)-1H-indole |
| 39 | 6-Methyl-3-(4-methyl-2-piperazin-1-yl-phenylsulfanyl)-1H-indole |
| 40 | 2-Methyl-3-(4-methyl-2-piperazin-1-yl-phenylsulfanyl)-1H-indole |
| 41 | 5-Methyl-3-(4-methyl-2-piperazin-1-yl-phenylsulfanyl)-1H-indole |
| 42 | 7-Methyl-3-(4-methyl-2-piperazin-1-yl-phenylsulfanyl)-1H-indole |
| 44 | 3-(2-Piperidin-4-yl-phenylsulfanyl)-1H-indole |
| 45 | 2-Methyl-3-(2-piperidin-4-yl-phenylsulfanyl)-1H-indole |
| 46 | 1-Methyl-3-(2-piperidin-4-yl-phenylsulfanyl)-1H-indole |
| 47 | 5-Methyl-3-(2-piperidin-4-yl-phenylsulfanyl)-1H-indole |
| 48 | 7-Fluoro-3-(2-piperidin-4-yl-phenylsulfanyl)-1H-indole |
| 49 | 6-Fluoro-3-(2-piperidin-4-yl-phenylsulfanyl)-1H-indole |
| 50 | 5-Methoxy-4-methyl-3-(2-piperidin-4-yl-phenylsulfanyl)-1H-indole |
| 51 | 4-Fluoro-3-(2-piperidin-4-yl-phenylsulfanyl)-1H-indole |
| 52 | 7-Methyl-3-(2-piperidin-4-yl-phenylsulfanyl)-1H-indole |
| 53 | 4-Methyl-3-(2-piperidin-4-yl-phenylsulfanyl)-1H-indole |
| 54 | 4-Chloro-3-(2-piperidin-4-yl-phenylsulfanyl)-1H-indole |
| 55 | 6-Chloro-3-(2-piperidin-4-yl-phenylsulfanyl)-1H-indole |
| 56 | 5-Fluoro-3-(2-piperidin-4-yl-phenylsulfanyl)-1H-indole |
| 57 | 5-Methoxy-3-(2-piperidin-4-yl-phenylsulfanyl)-1H-indole |
| 58 | 5-Chloro-3-(2-piperidin-4-yl-phenylsulfanyl)-1H-indole |
| 59 | 7-Methoxy-3-(2-piperidin-4-yl-phenylsulfanyl)-1H-indole |
| 60 | 7-Chloro-3-(2-piperidin-4-yl-phenylsulfanyl)-1H-indole |
| 61 | 7-Ethyl-3-(2-piperidin-4-yl-phenylsulfanyl)-1H-indole |
| 62 | 3-Methyl-2-(2-piperidin-4-yl-phenylsulfanyl)-1H-indole |
| 63 | 6-Methyl-3-(2-piperidin-4-yl-phenylsulfanyl)-1H-indole |
| 64 | 5-Fluoro-2-methyl-3-(2-piperidin-4-yl-phenylsulfanyl)-1H-indole | as the free base or a salt thereof. Each of these compounds is considered a specific embodiment and may be subjected to individual claims.

The present invention comprises the free base and salts of the compounds of the invention, typically, pharmaceutically acceptable salts. The salts of the invention include acid addition salts, metal salts, ammonium and alkylated ammonium salts.

The salts of the invention are preferably acid addition salts. The acid addition-salts of the invention are preferably pharmaceutically acceptable salts of the compounds of the invention formed with non-toxic acids. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Also intended as acid addition salts are the hydrates, which the present compounds, are able to form.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centre and it is intended that any optical isomers (i.e. enantiomers or diastereomers), as separated, pure or partially purified optical isomers and any mixtures thereof including racemic mixtures, i.e. a mixture of stereoisomers, are included within the scope of the invention Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials, or by stereoselective synthesis.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula I, IA, IB, IC, ID or IE, which are readily convertible in vivo into the required compound of the formula I, IA, IB, IC, ID or IE. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Some compounds according to the invention inhibit the serotonin transporter and are thus serotonin reuptake inhibitors. Typically, the compounds have an in vitro uptake inhibition (IC50) of 5 µM or less, typically of 1 µM or less, preferably less than 500 nM or less than 100 nM or less than 50 nM, preferably as measured by the method described in Example 3—Measurements of "[$^3$H]-5-HT uptake into rat cortical synaptosomes".

Some compounds according to the invention inhibit the norepinephrine transporter and are thus norepinephrine reuptake inhibitors. The compounds typically have an in vitro uptake inhibition (IC50) of 5 µM or less, typically of 1 µM or less, preferably less than 500 nM, less than 100 nM or less than 50 nM, as measured by the method described in Example 3—Measurements of "[$^3$H]noradrenaline uptake into rat cortical synaptosomes".

Some compounds according to the invention inhibit the dopamine transporter and are thus dopamine reuptake inhibitors. Typically, such compounds have an in vitro uptake inhibition (IC50) of 5 µM or less, typically of 1 µM or less, preferably less than 500 nM, less than 100 nM or less than 50 nM, preferably as measured by the method described in Example 3—"Measurements of [$^3$H]dopamine uptake into rat cortical synaptosomes".

As already mentioned, the compounds according to the invention are serotonin reuptake inhibitors and they are thus considered to be applicable in the treatment of one or more of the following disorders: affective disorders, pain disorders, ADHD and stress urinary incontinence.

An embodiment concerns compounds of the invention having dual action being serotonin reuptake inhibitors and dopamine reuptake inhibitors at the same time. Typically, compounds according to the invention having dual action have an in vitro uptake inhibition for the serotonin transporter which is at least 5, preferably at least 10 or even more preferred at least 20 or 30 times higher than the in vitro uptake inhibition for the dopamine transporter as measured by the methods described in Example 3—"Measurements of [$^3$H]-5-HT uptake into rat cortical synaptosomes" and "Measurements of [$^3$H]dopamine uptake into rat cortical synaptosomes".

An embodiment concerns compounds of the invention having dual action being serotonin reuptake inhibitors and norepinephrine reuptake inhibitors at the same time. Typically, compounds according to the invention having dual action have an in vitro uptake inhibition for the serotonin transporter which is at least 5, preferably at least 10 or even more preferred at least 20 or 30 times higher than the in vitro uptake inhibition for the norepinephrine transporter as measured by the methods described in Example 3—"Measurements of [$^3$H]-5-HT uptake into rat cortical synaptosomes" and "Measurements of [$^3$H]noradrenaline uptake into rat cortical synaptosomes".

A further embodiment concerns compounds of the invention having triple action and thus being serotonin reuptake inhibitors, norepinephrine reuptake inhibitors and dopamine reuptake inhibitors.

In a further aspect the invention provides a compound of formula I, IA, IB, IC, ID or IE as the free base or a salt thereof for use as a medicament.

An embodiment of the invention provides a pharmaceutical composition comprising a compound of formula I, IA, IB, IC, ID or IE as the free base or a salt thereof and at least one pharmaceutically acceptable carrier or diluent. The composition may comprise any one of the embodiments of formula I, IA, IB, IC, ID or IE described above.

A further embodiment of the invention relates to the use of a compound of formula I, IA, IB, IC, ID or IE as the free base or a salt thereof for the preparation of a pharmaceutical composition for the treatment of a disease or disorder wherein a serotonin reuptake inhibitor is beneficial. Such pharmaceutical composition may comprise any one of the embodiments of formula I, IA, IB, IC, ID or IE described above.

A further embodiment of the invention relates to the use of a compound of formula I, IA, IB, IC, ID or IE as the free base or a salt thereof for the preparation of a pharmaceutical composition for the treatment of a disease or disorder, wherein a combined serotonin and norepinephrine reuptake inhibitor is beneficial. Such pharmaceutical composition may comprise any one of the embodiments of formula I, IA, IB, IC, ID or IE described above.

A further embodiment of the invention relates to the use of a compound of formula I, IA, IB, IC, ID or IE as the free base or a salt thereof for the preparation of a pharmaceutical composition for the treatment of a disease or disorder, wherein a combined serotonin and dopamine reuptake inhibitor is beneficial. Such pharmaceutical composition may comprise any one of the embodiments of formula I, IA, IB, IC, ID or IE described above.

A further embodiment of the present invention relates to the use of a compound of formula I, IA, IB, IC, ID or IE as the free base or a salt thereof for the preparation of a pharmaceutical composition for the treatment of a disease or disorder, wherein a combined serotonin, norepinephrine and dopamine reuptake inhibitor is beneficial. Such pharmaceutical composition may comprise any one of the embodiments of formula I, IA, IB, IC, ID or IE described above.

A further embodiment of the invention relates to the use of a compound of formula I, IA, IB, IC, ID or IE as the free base or a salt thereof for the preparation of a pharmaceutical composition for the treatment of affective disorders, pain disorders, ADHD and stress urinary incontinence.

In a further embodiment the present invention relates to the use of a compound of formula I, IA, IB, IC, ID or IE as the free base or a salt thereof for the preparation of a pharmaceutical composition for the treatment of affective disorders. To further illustrate without limiting the invention, the affective disorder to be treated is selected from the group consisting of depressive disorders and anxiety disorders.

A further embodiment concerns the use of a compound of formula I, IA, IB, IC, ID or IE as the free base or a salt thereof for the preparation of a pharmaceutical composition for the treatment of depressive disorders. Typically, the depressive disorder to be treated is selected from the group consisting of major depressive disorder, postnatal depression, dysthymia and depression associated with bipolar disorder, alzheimers, psychosis or parkinsons. To further illustrate without limiting the invention, an embodiment of the invention concerns the treatment of major depressive disorder; another embodiment concerns the treatment of postnatal depression; another embodiment concerns the treatment of dysthymia; another embodiment concerns the treatment of depression associated with bipolar disorder, alzheimers, psychosis or parkinsons. To further illustrate without limiting the invention, an embodiment of the invention concerns the treatment of depression associated with bipolar disorder; another embodiment concerns the treatment of depression associated with alzheimers; another embodiment concerns the treatment of depression associated with psychosis; another embodiment concerns the treatment of depression associated with parkinsons.

A further embodiment concerns the use of a compound of formula I, IA, IB, IC, ID or IE as the free base or a salt thereof for the preparation of a pharmaceutical composition for the treatment of anxiety disorders. Typically, the anxiety disorders to be treated are selected from the group consisting of general anxiety disorder, social anxiety disorder, post traumatic stress disorder, obsessive compulsive disorder, panic disorder, panic attacks, specific phobias, social phobia and agoraphobia. To further illustrate without limiting the invention, an embodiment of the invention concerns the treatment of general anxiety disorder; another embodiment concerns the treatment of social anxiety disorder; another embodiment concerns the treatment of post traumatic stress disorder; another embodiment concerns the treatment of obsessive compulsive disorder; another embodiment concerns the treatment of panic disorder; another embodiment concerns the treatment of panic attacks; another embodiment concerns the treatment of specific phobias; another embodiment concerns the treatment of social phobia; another embodiment concerns the treatment of agoraphobia.

In a further embodiment the present invention relates to the use of a compound of formula I, IA, IB, IC, ID or IE as the free base or a salt thereof for the preparation of a pharmaceutical composition for the treatment of pain disorders. To further illustrate without limiting the invention, the pain disorder to be treated is selected from the group consisting of fibromyalgia syndrome (FMS), overall pain, back pain, shoulder pain, headache as well as pain while awake and during daily activities. To further illustrate without limiting the invention, an embodiment of the invention concerns the treatment of fibromyalgia syndrome; another embodiment concerns the treatment of overall pain; another embodiment concerns the treatment of back pain; another embodiment concerns the treatment of shoulder-pain; another embodiment concerns the treatment of headache; another embodiment concerns the treatment of pain while awake and during daily activities.

In a further embodiment the present invention relates to the use of a compound of formula I, IA, IB, IC, ID or IE as the free base or a salt thereof for the preparation of a pharmaceutical composition for the treatment of attention deficit hyperactivity disorder.

In a further embodiment the present invention relates to the use of a compound of formula I, IA, IB, IC, ID or IE as the free base or a salt thereof for the preparation of a pharmaceutical composition for the treatment of stress urinary incontinence.

The term "treatment" as used herein in connection with a disease or disorders includes also prevention as the case may be.

In a further aspect, the present invention relates to a method of preparing a compound of formula I, comprising deprotection or cleavage from a polymer support of a compound of formula VA or VB

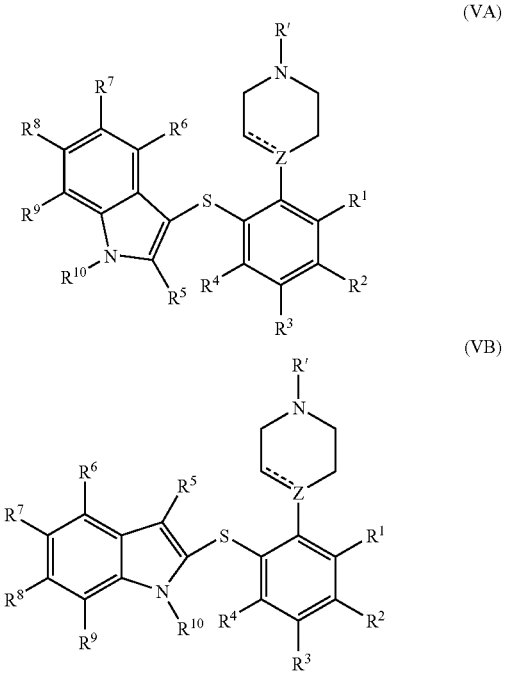

wherein Z, the dotted line and $R^1$-$R^{10}$ are as previously described, and $R^1$ is a carbamate or a benzyl-derived protective group.

Pharmaceutical Compositions

The present invention also relates to a pharmaceutical composition. The compounds of the invention as the free base or the salt thereof may be administered alone or in combination with pharmaceutically acceptable carriers or diluents, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

The pharmaceutical compositions formed by combining the compound of the invention and the pharmaceutical acceptable carriers are then readily administered in a variety of dosage forms suitable for the disclosed routes of administration. The formulations may conveniently be presented in unit dosage form by methods known in the art of pharmacy.

The compounds of this invention are generally utilized as the free substance (base) or as a pharmaceutically acceptable salt thereof. One example is an acid addition salt of a compound having the utility of a free base. When a compound of the invention contains a free base such salts are prepared in a conventional manner by treating a solution or suspension of a free base of the invention with a chemical equivalent of a pharmaceutically acceptable acid. Representative examples are mentioned above.

Pharmaceutical compositions for oral administration may be solid or liquid. Solid dosage forms for oral administration include e.g. capsules, tablets, dragees, pills, lozenges, powders, granules and tablette e.g. placed in a hard gelatine capsule in powder or pellet form or e.g. in the form of a troche or lozenge. Where appropriate, pharmaceutical compositions for oral administration may be prepared with coatings such as enteric coatings or they can be formulated so as to provide controlled release of the active ingredient such as sustained or prolonged release according to methods well known in the art. Liquid dosage forms for oral administration include e.g. solutions, emulsions, suspensions, syrups and elixirs.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid, lower alkyl ethers of cellulose, corn starch, potato starch, gums and the like. Examples of liquid carriers are syrup, peanut oil, olive oil, phospho lipids, fatty acids, fatty acid amines, polyoxyethylene and water.

The carrier or diluent may include any sustained release material known in the art, such as glyceryl monostearate or glyceryl distearate, alone or mixed with a wax.

Any adjuvants or additives usually used for such purposes such as colourings, flavourings, preservatives etc. may be used provided that they are compatible with the active ingredients.

The amount of solid carrier may vary but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents and subsequently compressing the mixture in a conventional tabletting machine.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.01 to about 1000 mg, such as about 0.01 to 100 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

Typical examples of recipes for the formulation of the invention are as follows:

1) Tablets containing 5.0 mg of a compound of the invention calculated as the free base:

| | |
|---|---|
| Compound of the invention | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound of the invention | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| | |
|---|---|
| Compound of the invention | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |

-continued

| | |
|---|---|
| Flavour | 0.05 mg |
| Saccharin sodium | 0.5 mg |
| Water | ad 1 mL |

4) Solution for injection containing per millilitre:

| | |
|---|---|
| Compound of the invention | 0.5 mg |
| Sorbitol | 5.1 mg |
| Acetic Acid | 0.05 mg |
| Saccharin sodium | 0.5 mg |
| Water | ad 1 mL |

By the expression a compound of the invention is meant any one of the embodiments of formula I, IA, IB, IC, ID and IE as described herein.

In a further aspect the present invention relates to a method of preparing a compound of the invention as described in the following.

Methods of Preparation of the Compounds of the Invention

The compounds of the invention may be prepared as follows:

Deprotection or cleavage from a polymer support of a compound of formula VA or VB wherein Z, the dotted line and $R^1$-$R^{10}$ are as previously described, and R' is a carbamate (such as methyl-, ethyl-, tert-butyl-, allyl-, or benzyl-carbamate) or a benzyl-derived protective group, wherein the protective groups may be linked to a solid support, like the Wang resin-based carbamate linker, whereupon the compound of formula I is isolated as the free base or an acid addition salt thereof.

The deprotection according to "Methods of preparation of the compounds of the invention" was performed by standard techniques, known to the persons skilled in the art and detailed in the textbook *Protective Groups in Organic Synthesis* Greene and Wuts, Wiley Interscience, (1991), ISBN 0471623016. The cleavage from a polymer support, such as from the Wang resin based carbamate linker, according to method A) was performed according to literature known procedures (Zaragoza *Tetrahedron Lett.* 1995, 36, 8677-8678 and Conti et al. *Tetrahedron Lett.* 1997, 38, 2915-2918).

Intermediates of formula VA and VB can be prepared by the following methods: Method A Chemical transformation of a substituted thiophenol compound of formula VIA or of a substituted diphenyl disulfide compound of formula VIB to the corresponding benzenesulfenyl chloride compound and subsequent reaction with an indole of formula VIII or IX gives the protected intermediates VA or VB, respectively.

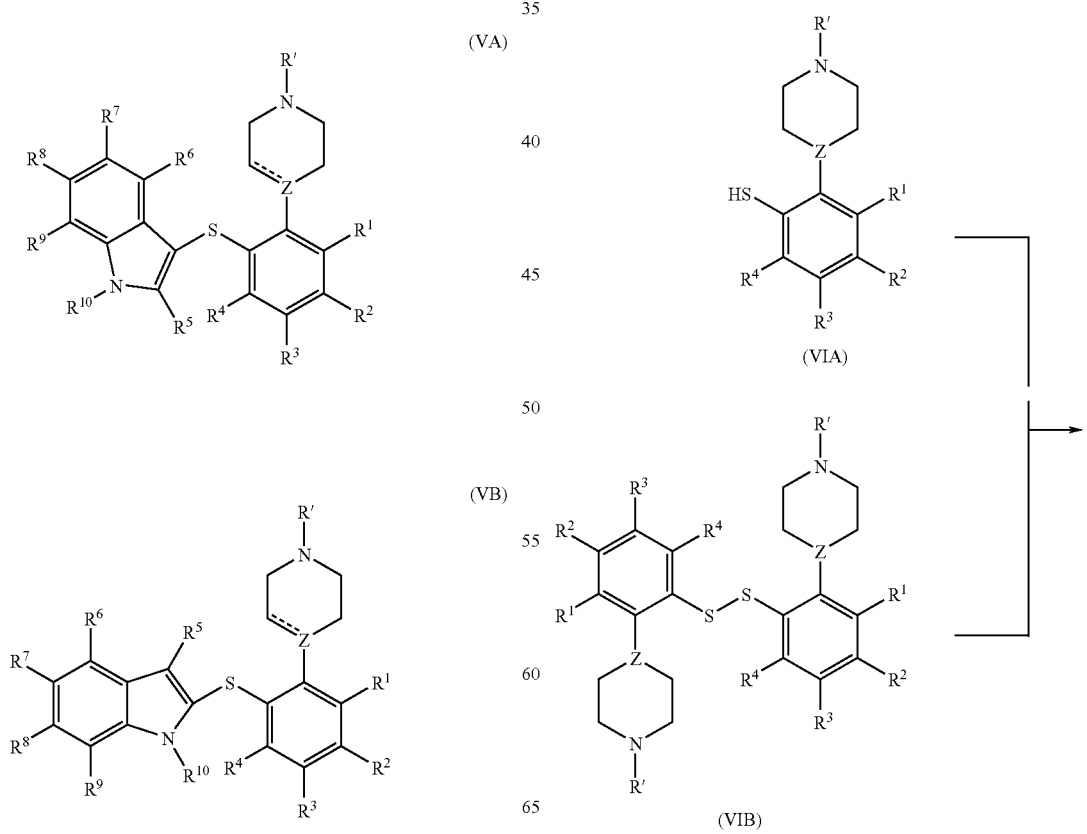

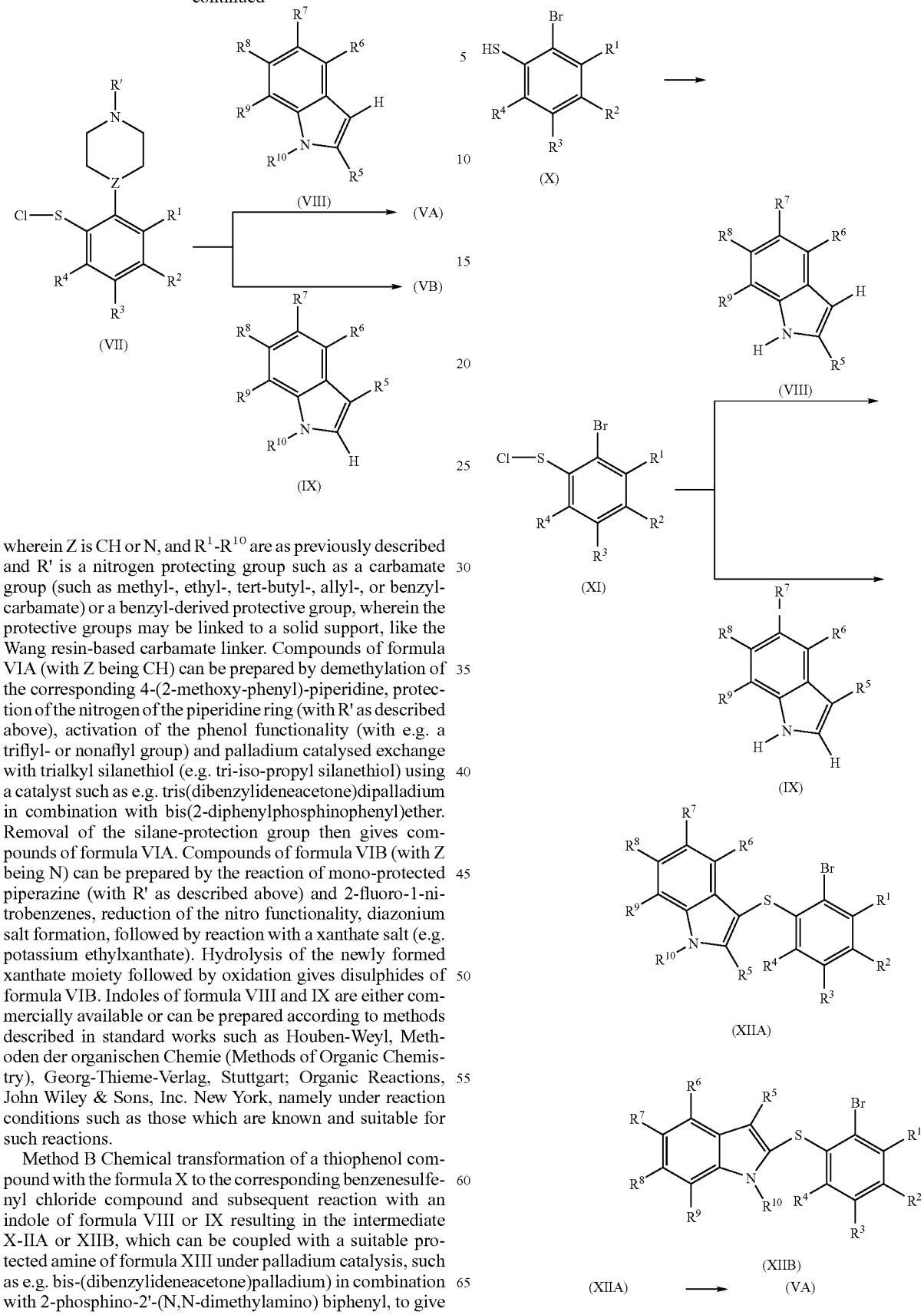

wherein Z is CH or N, and R$^1$-R$^{10}$ are as previously described and R' is a nitrogen protecting group such as a carbamate group (such as methyl-, ethyl-, tert-butyl-, allyl-, or benzyl-carbamate) or a benzyl-derived protective group, wherein the protective groups may be linked to a solid support, like the Wang resin-based carbamate linker. Compounds of formula VIA (with Z being CH) can be prepared by demethylation of the corresponding 4-(2-methoxy-phenyl)-piperidine, protection of the nitrogen of the piperidine ring (with R' as described above), activation of the phenol functionality (with e.g. a triflyl- or nonaflyl group) and palladium catalysed exchange with trialkyl silanethiol (e.g. tri-iso-propyl silanethiol) using a catalyst such as e.g. tris(dibenzylideneacetone)dipalladium in combination with bis(2-diphenylphosphinophenyl)ether. Removal of the silane-protection group then gives compounds of formula VIA. Compounds of formula VIB (with Z being N) can be prepared by the reaction of mono-protected piperazine (with R' as described above) and 2-fluoro-1-nitrobenzenes, reduction of the nitro functionality, diazonium salt formation, followed by reaction with a xanthate salt (e.g. potassium ethylxanthate). Hydrolysis of the newly formed xanthate moiety followed by oxidation gives disulphides of formula VIB. Indoles of formula VIII and IX are either commercially available or can be prepared according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known and suitable for such reactions.

Method B Chemical transformation of a thiophenol compound with the formula X to the corresponding benzenesulfenyl chloride compound and subsequent reaction with an indole of formula VIII or IX resulting in the intermediate X-IIA or XIIB, which can be coupled with a suitable protected amine of formula XIII under palladium catalysis, such as e.g. bis-(dibenzylideneacetone)palladium) in combination with 2-phosphino-2'-(N,N-dimethylamino) biphenyl, to give the compounds VA or VB.

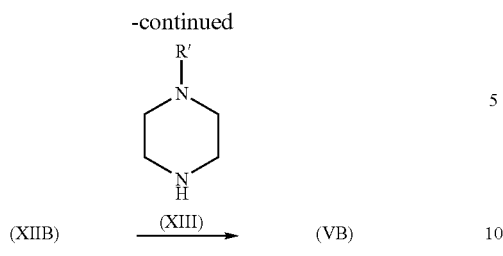

wherein Z is nitrogen, $R^1$-$R^{10}$ are as previously described and R' is a carbamate (such as methyl-, ethyl-, tert-butyl-, allyl-, or benzyl-carbamate) or a benzyl-derived protective group, wherein the protective groups may be linked to a solid support, like the Wang resin-based carbamate linker.

Method C Chemical transformation of a thiophenol compound with the formula X to the corresponding benzenesulfenyl chloride compound and subsequent reaction with an indole of formula VIII or IX resulting in the intermediate XIIA or XIIB, which can be coupled with a suitable protected amine boronic acid ester of formula XIV under palladium catalysis to give the compounds VA or VB using a catalyst such as e.g. 1,1'-bis(diphenylphosphino)ferrocenedichloropalladium(II).

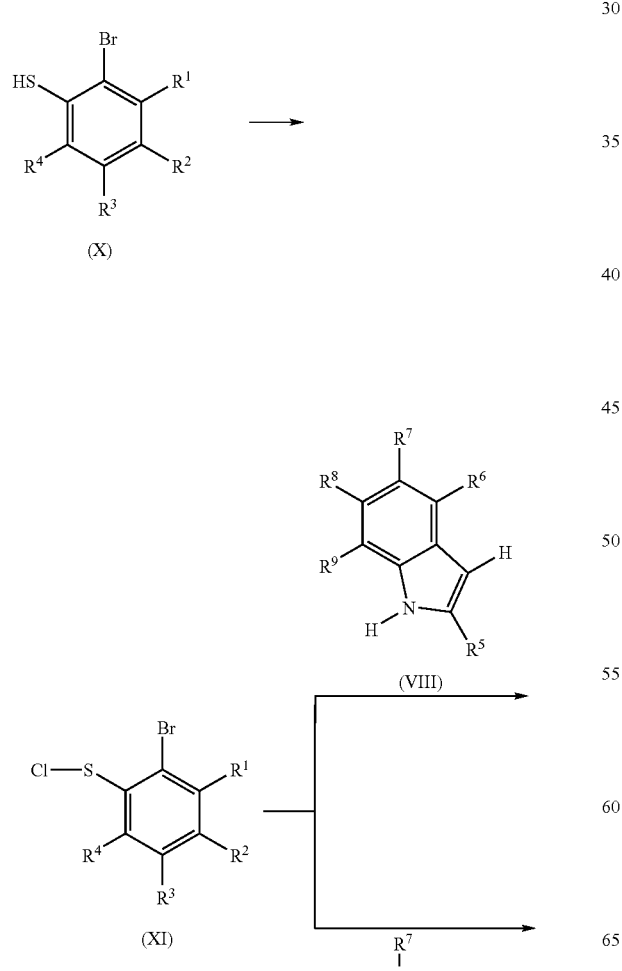

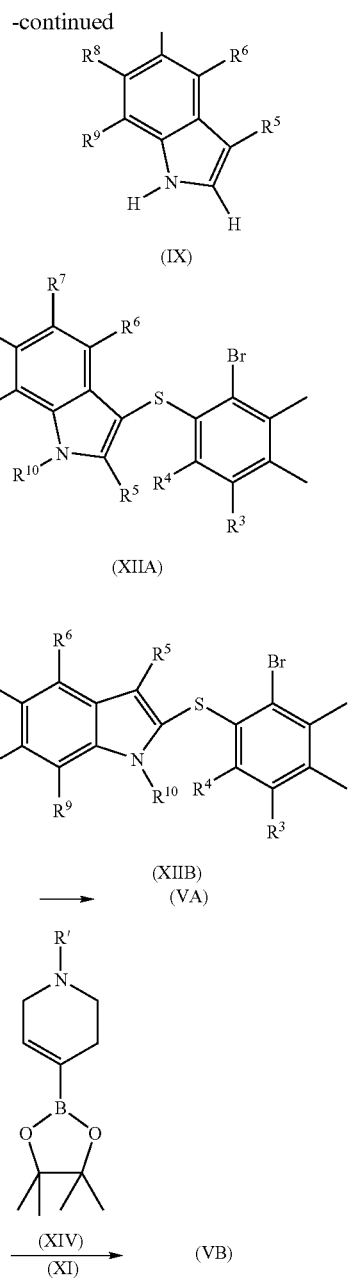

wherein Z is C, the dotted line represents a bond, $R^1$-$R^{10}$ are as previously described and R' is a carbamate (such as methyl-, ethyl-, tert-butyl-, allyl-, or benzyl-carbamate) or a benzyl-derived protective group, wherein the protective groups may be linked to a solid support, like the Wang resin-based carbamate linker.

Method D Reduction of a tetrahydropyridine compound of formula VA (in which Z is C and the dotted line represents a bond) to the corresponding piperidine compound of formula VA (in which Z is CH), and reduction of a tetrahydropyridine compound of formula VB (in which Z is C and the dotted line represents a bond) to the corresponding piperidine compound of formula VB (in which Z is CH). Subsequently the compound of formula I is isolated as the free base or an acid addition salt thereof.

The invention disclosed herein is further illustrated by the following non-limiting examples.

EXAMPLES

General Methods

Analytical LC-MS data were obtained on a PE Sciex API 150EX instrument equipped with photoionization (APPI) ion source and Shimadzu LC-8A/SLC-10A LC system. The LC conditions (Symmetry C18 column 4.6×30 mm with a particle size of 3.5 μm) were linear gradient elution with eluents A (water containing 0.05% TFA) and B (acetonitrile containing 5% water and 0.035% TFA). Gradient (time[min]/% B): (0.00/10.0); (4.00/100.0); (4.10/10.0); (5.00/10.0) with 2 mL/min. Purity was determined by integration of the UV trace (254 nm) and ELS (SEDERE SEDEX 55 with Heto CBN 8-30 cooling bath). The retention times, $R_t$, are expressed in minutes.

Mass spectra were obtained by an alternating scan method to give molecular weight information. The molecular ion, MH+, was obtained at low orifice voltage (5V) and fragmentation at high orifice voltage (100V).

Preparative LC-MS-separation was performed on the same instrument. The LC conditions (Symmetry C18 column 10×50 mm) were linear gradient elution with eluents A (water containing 0.05% TFA) and B (acetonitrile containing 5% water and 0.035% TFA): (time[min]/% B): (0.00/20.0); (7.00/100.0); (7.10/20.0); (8.00/20.0) with 5.7 mL/min Fraction collection was performed by split-flow MS detection.

For column chromatography silica gel of type Kieselgel 60, 230-400 mesh ASTM was used. For ion-exchange chromatography (SCX, 1 g, Varian Mega Bond Elut®, Chrompack cat. No. 220776) was used. Prior use of the SCX-columns was pre-conditioned with 10% solution of acetic acid in methanol (3 mL).

Preparation of Intermediates

4-(2-Methoxy-phenyl)-piperidine (Method A)

Purchased from Maybridge (Product Number BTB 13447)

4-(2-Hydroxy-phenyl)-piperidine-1-carboxylic acid tert-butyl ester (Method A)

BBr$_3$ (7.0 mL; 74 mmol) was added slowly to 4-(2-methoxy-phenyl)-piperidine (6.25 g; 32.7 mmol) in 100 dichloromethane at 0° C. under argon. The reaction mixture was allowed to warm to room temperature and stirred 16 hours. The reaction mixture was quenched by carefully adding 100 mL water at 0° C. Another 300 mL water was added, followed by the addition of 50 mL 28% aqueous NaOH. The organic phase was discarded. Di-tert-butyl dicarbonate (9.0 g; 41 mmol) was added to the aqueous phase. The reaction mixture was stirred 1 hour at room temperature, neutralized with 1 N HCl, extracted with ethyl acetate (2×200 mL). The organic phase was washed with brine (100 mL), dried with MgSO$_4$ and concentrated in vacuo to give 4-(2-hydroxy-phenyl)-piperidine-1-carboxylic acid tert-butyl ester.

4-[2-(Nonafluorobutane-1-sulfonyloxy)-phenyl]-piperidine-1-carboxylic acid tert-butyl ester (Method A)

Nonafluoro-butane-1-sulfonyl fluoride (2.71 mL; 15.1 mmol) was added to a mixture of ethyl-diisopropyl-amine (2.87 mL; 16.5 mmol), 4-(N,N-dimethylamino)-pyridine (25 mg) and 4-(2-hydroxy-phenyl)-piperidine-1-carboxylic acid tert-butyl ester (3.81 g; 13.7 mmol) in 50 ml 1,2-dichloroethane at 0° C. under argon. The reaction mixture was allowed to warm to room temperature and stirred 16 hours. The reaction mixture was extracted with water (100 mL) and brine (100 mL). The combined aqueous phases were extracted with ethyl acetate (100 mL). The combined organic phases were washed with brine (100 mL), dried with MgSO$_4$ and concentrated in vacuo. The residue was purified by flash chromatography (silica gel; ethyl acetate/heptane) to give 4.34 g 4-[2-(nonafluorobutane-1-sulfonyloxy)-phenyl]-piperidine-1-carboxylic acid tert-butyl ester (7.76 mmol; 57%).

4-(2-Triisopropylsilanylsulfanyl-phenyl)-piperidine-1-carboxylic acid tert-butyl ester (Method A)

Bis[(2-diphenylphosphino)phenyl]ether (0.43 g; 0.80 mmol) and tris(dibenzylideneacetone)-dipalladium (0.37 mg; 0.40 mmol) were dissolved in 40 mL toluene. 4-[2-(Nonafluorobutane-1-sulfonyloxy)-phenyl]-piperidine-1-carboxylic acid tert-butyl ester (4.34 g; 7.76 mmol), triisopropyl-silanethiol (1.83 mL; 8.53 mmol) and sodium tert-butoxide (0.90 g; 9.3 mmol) were added and the reaction mixture was stirred under argon for 3 hours at 100° C. The reaction mixture was cooled to room temperature filtered through a pad of silica and concentrated in vacuo. The residue was purified by flash chromatography (silica gel; ethyl acetate/heptane) to give 1.58 g 4-(2-triisopropylsilanylsulfanyl-phenyl)-piperidine-1-carboxylic acid tert-butyl ester (3.51 mmol; 45%).

4-(5-Methyl-2-nitro-phenyl)-piperazine-1-carboxylic acid benzyl ester (Method A)

Piperazine-1-carboxylic acid benzyl ester (8.00 g; 36.3 mmol), 2-fluoro-4-methyl-1-nitro-benzene (4.70 g; 30.3 mmol) and potassium carbonate (8.5 g; 61.5 mmol) were stirred 3 hours in 50 mL DMSO at 80° C. The reaction mixture was cooled to room temperature and 250 mL Water was added. The mixture was extracted with diethyl ether (2×250 mL). The organic phase was washed with water (100 mL), 1 N HCl (2×100 mL), brine (2×100 mL), dried with MgSO$_4$ and concentrated in vacuo to give 10.5 g (29.5 mmol; 97.6%) 4-(5-methyl-2-nitro-phenyl)-piperazine-1-carboxylic acid benzyl ester.

4-(2-Amino-5-methyl-phenyl)-piperazine-1-carboxylic acid benzyl ester (Method A)

4-(5-Methyl-2-nitro-phenyl)-piperazine-1-carboxylic acid benzyl ester (5.60 g; 15.7 mmol) and SnCl$_2$.H$_2$O (17.5 g; 77.6 mmol) were refluxed in 100 mL ethanol for 2½ hours. Ethanol was removed in vacuo. The residue was poured into 300 mL saturated NaHCO$_3$. The mixture was extracted with ethyl acetate (2×250 mL). The organic phase was washed with brine (2×100 mL), dried with MgSO$_4$, filtered through a pad of silica and concentrated in vacuo to give 4.71 g (14.5 mmol; 91.6%) 4-(2-amino-5-methyl-phenyl)-piperazine-1-carboxylic acid benzyl ester.

2-(4-(Benzyloxy-carbonyl)-piperazin-1-yl)-4-methyl-benzenedisulphide (Method A)

Sulphuric acid (2.37 g; 24.2 mmol) in 20 mL of water was added to 4-(2-amino-5-methyl-phenyl)-piperazine-1-carboxylic acid benzyl ester in 20 mL THF. THF was removed in vacuo. The mixture was cooled to 0° C. and NaNO₂ (0.611 g; 8.86 mmol) in 10 mL water was added dropwise. The reaction mixture was stirred 15 minutes at room temperature and added dropwise to potassium ethylxanthate (3.87 g; 24.2 mmol) in 30 mL water at 70° C. (CAUTION!: gas evolution). The reaction mixture was stirred 2 hours at 70° C. 10 mL 28% NaOH and 30 mL ethanol were added and the reaction mixture was stirred 16 hours at 60° C. in an open flask. The reaction mixture was cooled to room temperature and extracted with diethyl ether (2×250 mL). The organic phase was washed with brine (2×100 mL), dried with MgSO₄ and concentrated in vacuo. The residue was purified by flash chromatography (silica gel; ethyl acetate/heptane) to give 1.19 g 2-(4-(benzyloxy-carbonyl)-piperazin-1-yl)-4-methyl-benzenedisulphide (1.74 mmol; 43%).

2-(4-(Benzyloxy-carbonyl)-piperazin-1-yl)-benzenedisulphide (Method A) was prepared in a similar way.

3-(2-Bromo-phenylsulfanyl)-1H-indole (Method B, C)

69.9 mmol of N-chlorosuccinimide was suspended in 200 mL dry CH₂Cl₂ and cooled in an ice bath to 0° C. It was slowly treated with 66.6 mmol 2-bromothiophenol. After addition was completed the solution cleared up and turned orange. Stirring was continued at room temperature for 1 hour.

The above solution was added slowly to a solution of 66.6 mmol indole in 180 mL dry DMF at 0° C. under argon. After addition was completed the solution was stirred for 2½ hour at 0° C.

The reaction was quenched with 200 mL water, and 150 mL sat. NaHCO₃ was added. 250 mL ethyl acetate was added and the phases were separated. The water phase was back extracted with ethyl acetate. The combined organic phases were then washed with brine, dried over MgSO₄ and evaporated under vacuum. The title compound was recrystallized from acetonitrile.

3-(2-Bromo-phenylsulfanyl)-indole-1-carboxylic acid tert-butyl ester (Method B, C)

To a solution of 26.3 mmol 3-(2-bromo-phenylsulfanyl)-1H-indole in dry CH₂Cl₂ (120 mL) was added 1.3 mmol of 4-dimethyl aminopyridine and 28.9 of mmol triethylamine. 28.9 mmol of di-tert-butyl-dicarbonate were added and the solution was stirred at room temperature over night under argon. The solution was washed with 0.5 M aqueous HCl. The water phase was extracted with CH₂Cl₂. The combined organic phase was dried over K₂CO₃ and evaporated under vacuum. The compound was applied to a silica column in 1/4 ethyl acetate/heptane and filtered through using 1/4 ethyl acetate/heptane. The eluent was evaporated under vacuum to give the title compound.

3-[2-(4-tert-Butoxycarbonyl-piperazin-1-yl)-phenyl-sufanyl]-indole-1-carboxylic acid tert-butyl ester (Method B)

0.0086 mmol of Pd(dba)₂ (bis-(dibenzylideneacetone)palladium) and 0.0172 mmol of 2-phosphino-2'-(N,N-dimethylamino) biphenyl were added to a dry flask and stored under argon.

0.043 mmol of 3-(2-bromo-phenylsulfanyl)-indole-1-carboxylic acid tert-butyl ester and 0.052 mmol of N-tert-butoxycarbonyl-piperazine were dissolved in 2.5 mL dry toluene and 0.061 mmol sodium-tert-butoxide in toluene were added. The solution was degassed and added to the flask with bis(dibenzylideneacetone)-palladium and of 2-phosphino-2'-(N,N-dimethylamino)biphenyl. The reaction was stirred for 18 hour at 100° C. Ethyl acetate (3 mL) was added and the organic phase was washed with aqueous NH₄Cl and brine, dried over MgSO₄ and evaporated under vacuum to give the title compound.

4-(4,4,5,5-Tetramethyl-[1,3,2]dioxaborolan-2-yl)-3,6-dihydro-2H-pyridine-1-carboxylic acid tert-butyl ester (Method C)

Was made according to the procedure described in Tetrahedron Letters 41 (2000) 3705-3708.

Example 1

Compounds of the Invention of Formula IA

Synthesis of 3-(2-piperazin-1-yl-phenylsulfanyl)-1H-indole

3 M HCl-gas in dry ethyl acetate (3 mL) was added to 3-[2-(4-tert-butoxycarbonyl-piperazin-1-yl)-phenylsulfanyl]-indole-1-carboxylic acid tert-butyl ester. The solution was stirred for 1 h at 0° C. and evaporated under vacuum. The crude product was purified by preparative LC-MS. The isolated product was submitted for testing as DMSO solution.

The following compounds were prepared in a similar way and analytical data are shown in table 1:
1. 3-(2-Piperazin-1-yl-phenylsulfanyl)-1H-indole
2. 4-Methoxy-3-(2-piperazin-1-yl-phenylsulfanyl)-1H-indole
3. 3-(2-Piperazin-1-yl-phenylsulfanyl)-1H-indole-7-carboxylic acid methyl ester
4. 5-Nitro-3-(2-piperazin-1-yl-phenylsulfanyl)-1H-indole
5. 6-Chloro-3-(2-piperazin-1-yl-phenylsulfanyl)-1H-indole
6. 6-Methoxy-3-(2-piperazin-1-yl-phenylsulfanyl)-1H-indole
7. 6-Fluoro-3-(2-piperazin-1-yl-phenylsulfanyl)-1H-indole
8. 7-Methyl-3-(2-piperazin-1-yl-phenylsulfanyl)-1H-indole
9. 3-[2-(1,2,3,6-Tetrahydro-pyridin-4-yl)-phenylsulfanyl]-1H-indole
11. 4-Fluoro-3-(2-piperazin-1-yl-phenylsulfanyl)-1H-indole
12. 5-Fluoro-3-(2-piperazin-1-yl-phenylsulfanyl)-1H-indole Example 2

Compounds of Formula IA or IB

Synthesis of 3-(2-Piperidin-4-yl-phenylsulfanyl)-1H-indole 1.58 g 4-(2-Triisopropylsilanylsulfanyl-phenyl)-piperidine-1-carboxylic acid tert-butyl ester (3.51 mmol) in 10 mL THF was added to 1.21 g tetrabutylammonium fluoride dihydrate (3.85 mmol) in 5 mL THF at 0° C. The reaction mixture was stirred 1 hour at 0° C., filtered through a plug of silica (eluted with EtOAc/heptane 1:1) and concentrated in vacuo. The residue was redissolved in 14 mL THF. 2 mL of this solution (≈0.5 mmol) was added to 67 mg N-chloro succinimide (0.50 mmol) in 2 mL 1,2-dichloro-ethane at 0° C. The reaction mixture was stirred 30 minutes at room temperature. The resulting solution was added to 90 mg indole (0.75 mmol) in 2 mL THF at 0° C. The reaction mixture was stirred 2 hour at 0° C., poured into 20 mL saturated NaHCO₃ and extracted with ethyl acetate (2×50 mL). The combined organic phases were washed with brine (20 mL), dried with MgSO₄ and concentrated in vacuo. The residue was purified by flash chromatography (silica gel; ethyl acetate/heptane) to give 89 mg 4-[2-(1H-indol-3-ylsulfanyl)-phenyl]-piperidine-1-carboxylic acid tert-butyl ester (0.22 mmol, ≈44%). 2 mL diethyl ether saturated with HCl was added to 4-[2-(1H-indol-3-ylsulfanyl)-phenyl]-piperidine-1-carboxylic acid tert-butyl ester and stirred over night at room temperature. The reaction mixture was neutralized with saturated NaHCO₃ and extracted with ethyl acetate (2×50 mL). The combined organic phases were washed with brine (20 mL), dried with MgSO₄ and concentrated in vacuo. 3-(2-piperidin-4-yl-phenylsulfanyl)-1H-indole was isolated after preparative HPLC.

The following compounds were prepared in a similar way and analytical data are shown in Table 1:

44. 3-(2-Piperidin-4-yl-phenylsulfanyl)-1H-indole
45. 2-Methyl-3-(2-piperidin-4-yl-phenylsulfanyl)-1H-indole
46. 1-Methyl-3-(2-piperidin-4-yl-phenylsulfanyl)-1H-indole
47. 5-Methyl-3-(2-piperidin-4-yl-phenylsulfanyl)-1H-indole
48. 7-Fluoro-3-(2-piperidin-4-yl-phenylsulfanyl)-1H-indole
49. 6-Fluoro-3-(2-piperidin-4-yl-phenylsulfanyl)-1H-indole
50. 5-Methoxy-4-methyl-3-(2-piperidin-4-yl-phenylsulfanyl)-1H-indole
51. 4-Fluoro-3-(2-piperidin-4-yl-phenylsulfanyl)-1H-indole
52. 7-Methyl-3-(2-piperidin-4-yl-phenylsulfanyl)-1H-indole
53. 4-Methyl-3-(2-piperidin-4-yl-phenylsulfanyl)-1H-indole
54. 4-Chloro-3-(2-piperidin-4-yl-phenylsulfanyl)-1H-indole
55. 6-Chloro-3-(2-piperidin-4-yl-phenylsulfanyl)-1H-indole
56. 5-Fluoro-3-(2-piperidin-4-yl-phenylsulfanyl)-1H-indole
57. 5-Methoxy-3-(2-piperidin-4-yl-phenylsulfanyl)-1H-indole
58. 5-Chloro-3-(2-piperidin-4-yl-phenylsulfanyl)-1H-indole
59. 7-Methoxy-3-(2-piperidin-4-yl-phenylsulfanyl)-1H-indole
60. 7-Chloro-3-(2-piperidin-4-yl-phenylsulfanyl)-1H-indole
61. 7-Ethyl-3-(2-piperidin-4-yl-phenylsulfanyl)-1H-indole
62. 3-Methyl-2-(2-piperidin-4-yl-phenylsulfanyl)-1H-indole Synthesis of 3-(4-Methyl-2-piperazin-1-yl-phenylsulfanyl)-1H-indole SO₂Cl₂ (120 µL; 1.50 mmol) was added to 2-(4-(benzyloxy-carbonyl)-piperazin-1-yl)-4-methyl-benzenedisulphide (0.956 g; 1.40 mmol) in 28 mL 1,2-dichloroethane and stirred 15 minutes at room temperature. 1 mL of this mixture was added to indole (23 mg; 0.20 mmol) in 1 mL THF at 0° C. under argon. The reaction mixture was stirred 2 hours at 0° C. 2 mL saturated NaHCO₃ and 2 mL ethyl acetate was added. The organic phase was separated and concentrated in vacuo. The residue was dissolved in 1 mL DMSO. 0.5 mL 20% aqueous KOH was added. The reaction mixture was stirred 4 minutes at 150° C. under microwave irradiation. 3 mL saturated aqueous NH₄Cl was added. The mixture was extracted with ethyl acetate (2×5 mL). The organic phase was concentrated in vacuo. 3-(4-Methyl-2-piperazin-1-yl-phenylsulfanyl)-1H-indole was isolated after preparative HPLC.

The following compounds were prepared in a similar way and analytical data are shown in Table 1:

10. 6-Methyl-3-(2-piperazin-1-yl-phenylsulfanyl)-1H-indole
13. 4-Methyl-3-(4-methyl-2-piperazin-1-yl-phenylsulfanyl)-1H-indole
14. 6-Fluoro-3-(4-methyl-2-piperazin-1-yl-phenylsulfanyl)-1H-indole
15. 4-Fluoro-3-(4-methyl-2-piperazin-1-yl-phenylsulfanyl)-1H-indole
16. 7-Fluoro-3-(4-methyl-2-piperazin-1-yl-phenylsulfanyl)-1H-indole
17. 5-Methoxy-4-methyl-3-(4-methyl-2-piperazin-1-yl-phenylsulfanyl)-1H-indole
18. 5-Methoxy-3-(4-methyl-2-piperazin-1-yl-phenylsulfanyl)-1H-indole
19. 7-Methoxy-3-(4-methyl-2-piperazin-1-yl-phenylsulfanyl)-1H-indole
20. 4-Methoxy-3-(4-methyl-2-piperazin-1-yl-phenylsulfanyl)-1H-indole
21. 4-Chloro-3-(4-methyl-2-piperazin-1-yl-phenylsulfanyl)-1H-indole
22. 7-Chloro-3-(4-methyl-2-piperazin-1-yl-phenylsulfanyl)-1H-indole
23. 1-Methyl-3-(4-methyl-2-piperazin-1-yl-phenylsulfanyl)-1H-indole
24. 3-Methyl-2-(4-methyl-2-piperazin-1-yl-phenylsulfanyl)-1H-indole
25. 2-Methyl-3-(2-piperazin-1-yl-phenylsulfanyl)-1H-indole
26. 5-Methyl-3-(2-piperazin-1-yl-phenylsulfanyl)-1H-indole
27. 4-Methyl-3-(2-piperazin-1-yl-phenylsulfanyl)-1H-indole
28. 7-Fluoro-3-(2-piperazin-1-yl-phenylsulfanyl)-1H-indole
29. 7-Ethyl-3-(2-piperazin-1-yl-phenylsulfanyl)-1H-indole
30. 5-Methoxy-4-methyl-3-(2-piperazin-1-yl-phenylsulfanyl)-1H-indole
31. 5-Methoxy-3-(2-piperazin-1-yl-phenylsulfanyl)-1H-indole
32. 7-Methoxy-3-(2-piperazin-1-yl-phenylsulfanyl)-1H-indole
33. 5-Fluoro-2-methyl-3-(2-piperazin-1-yl-phenylsulfanyl)-1H-indole
34. 5-Chloro-3-(2-piperazin-1-yl-phenylsulfanyl)-1H-indole
35. 4-Chloro-3-(2-piperazin-1-yl-phenylsulfanyl)-1H-indole
36. 7-Chloro-3-(2-piperazin-1-yl-phenylsulfanyl)-1H-indole
37. 1-Methyl-3-(2-piperazin-1-yl-phenylsulfanyl)-1H-indole
38. 3-Methyl-2-(2-piperazin-1-yl-phenylsulfanyl)-1H-indole
39. 6-Methyl-3-(4-methyl-2-piperazin-1-yl-phenylsulfanyl)-1H-indole
40. 2-Methyl-3-(4-methyl-2-piperazin-1-yl-phenylsulfanyl)-1H-indole
41. 5-Methyl-3-(4-methyl-2-piperazin-1-yl-phenylsulfanyl)-1H-indole
42. 7-Methyl-3-(4-methyl-2-piperazin-1-yl-phenylsulfanyl)-1H-indole

TABLE 1

Measured molecular mass, measured HPLC-retention time (RT, min) and UV- and ELSD-purities (%).

| compound | RT min. | UV-purity (%) | ELSD-purity (%) | M + H⁺ | Synthesis method |
|---|---|---|---|---|---|
| 1 | 2.04 | 98.3 | 65.3 | 310 | B |
| 2 | 1.77 | 100 | 91.3 | 340 | B |
| 3 | 1.93 | 100 | 93.42 | 368 | B |
| 4 | 1.82 | 90.5 | 57.96 | 355 | B |
| 5 | 2.005 | 98.69 | 93.33 | 346 | B |
| 6 | 1.78 | 98.43 | 97.6 | 340 | B |
| 7 | 1.875 | 99.24 | 89.92 | 328 | B |
| 8 | 1.92 | 95.03 | 98.24 | 324 | B |
| 9 | 2 | 93.16 | 77.61 | 307.1 | C |
| 10 | 2.017 | 73.77 | 96.96 | 342.2 | A |
| 11 | 1.86 | 93.4 | 99.6 | 328 | B |

TABLE 1-continued

Measured molecular mass, measured HPLC-retention time (RT, min) and UV- and ELSD-purities (%).

| compound | RT min. | UV-purity (%) | ELSD-purity (%) | M + H$^+$ | Synthesis method |
|---|---|---|---|---|---|
| 12 | 2.04 | 96.06 | 97.98 | 328 | B |
| 13 | 2.335 | 91.77 | 95.19 | 338.3 | A |
| 14 | 2.3 | 84.45 | 99.8 | 341.9 | A |
| 15 | 2.213 | 74.5 | 95.49 | 341.8 | A |
| 16 | 2.302 | 83.07 | 98.83 | 342.0 | A |
| 17 | 2.37 | 79.23 | 94.36 | 398.1 | A |
| 18 | 2.193 | 72.02 | 88.95 | 354.2 | A |
| 19 | 2.282 | 81.72 | 94.25 | 354.0 | A |
| 20 | 2.185 | 71.34 | 93.84 | 354.2 | A |
| 21 | 2.3 | 82.42 | 96.53 | 358.0 | A |
| 22 | 2.442 | 82.34 | 98.28 | 358.0 | A |
| 23 | 2.435 | 84.72 | 96.25 | 338.0 | A |
| 24 | 2.568 | 87.44 | 97.55 | 338.3 | A |
| 25 | 1.913 | 91.99 | 99.79 | 324.1 | A |
| 26 | 1.983 | 74.46 | 95.27 | 323.9 | A |
| 27 | 1.967 | 82.68 | 100 | 324.1 | A |
| 28 | 1.928 | 96.71 | 99.85 | 328.1 | A |
| 29 | 2.137 | 71.62 | 99.05 | 338.3 | A |
| 30 | 1.92 | 75.46 | 100 | 354.2 | A |
| 31 | 1.815 | 70.05 | 88.36 | 340.0 | A |
| 32 | 1.907 | 74.16 | 93.41 | 340.1 | A |
| 33 | 1.965 | 94.37 | 99.87 | 342.0 | A |
| 34 | 2.047 | 93.32 | 100 | 344.1 | A |
| 35 | 2.04 | 95.23 | 99.88 | 344.1 | A |
| 36 | 2.078 | 94.53 | 100 | 344.1 | A |
| 37 | 2.07 | 95.53 | 100 | 324.0 | A |
| 38 | 2.213 | 95.06 | 99.92 | 324.1 | A |
| 39 | 2.02 | 79.43 | 98.47 | 338.3 | A |
| 40 | 2.03 | 80.36 | 95.66 | 338.3 | A |
| 41 | 2.09 | 77.01 | 98.45 | 338.1 | A |
| 42 | 2.108 | 84.83 | 99.76 | 338.3 | A |
| 44 | 1.933 | 93.78 | 99.68 | 309.1 | A |
| 45 | 1.995 | 91.34 | 99.51 | 323.1 | A |
| 46 | 2.133 | 98.98 | 99.47 | 323 | A |
| 47 | 2.06 | 87.52 | 98.71 | 323.1 | A |
| 48 | 2.012 | 91.07 | 98.64 | 327.2 | A |
| 49 | 2.008 | 95.96 | 98.6 | 326.9 | A |
| 50 | 1.963 | 83.51 | 98.37 | 354.2 | A |
| 51 | 1.937 | 88.63 | 97.5 | 327.2 | A |
| 52 | 2.072 | 95.08 | 97.16 | 323.1 | A |
| 53 | 2.013 | 89.2 | 97.12 | 323.1 | A |
| 54 | 1.987 | 79.17 | 96.72 | 342.9 | A |
| 55 | 2.158 | 92 | 95.27 | 342.9 | A |
| 56 | 1.987 | 94.53 | 95.17 | 327 | A |
| 57 | 1.9 | 78.75 | 94.62 | 339.1 | A |
| 58 | 2.042 | 88.63 | 87.81 | 342.9 | A |
| 59 | 1.985 | 90.24 | 80.44 | 339.3 | A |
| 60 | 2.108 | 95.87 | 99.68 | 342.9 | A |
| 61 | 2.177 | 73.11 | 98.96 | 337.2 | A |
| 62 | 2.242 | 95.29 | 98.7 | 323 | A |
| 63 | 1.987 | 92.82 | 99.65 | 323.1 | A |
| 64 | 1.958 | 75.72 | 95.59 | 341.1 | A |

Example 3

Transporter Inhibition Assay

Measurements of [$^3$H]-5-HT Uptake into Rat Cortical Synaptosomes

Whole brains from male Wistar rats (125-225 g), excluding cerebellum, are homogenized in 0.32 M sucrose supplemented with 1 mM nialamid with a glass/teflon homogenizer. The homogenate is centrifuged at 600× g for 10 min at 4° C. The pellet is discarded and the supernatant is centrifuged at 20.000× g for 55 min. The final pellet is homogenized (20 sec) in this assay buffer (0.5 mg original tissue/well). Test compounds (or buffer) and 10 nM [$^3$H]-5-HT are added to 96 well plates and shaken briefly. Composition of assay buffer: 123 mM NaCl, 4.82 mM KCl, 0.973 mM CaCl$_2$, 1.12 mM MgSO$_4$, 12.66 mM Na$_2$HPO$_4$, 2.97 mM NaH$_2$PO$_4$, 0.162 mM EDTA, 10 mM glucose and 1 mM ascorbic acid. Buffer is oxygenated with 95% O$_2$/5% CO$_2$ for 10 min at 37° C. and pH is adjusted 7.4. The incubation is started by adding tissue to a final assay volume of 0.2 mL. After 15 min incubation with radioligand at 37° C., samples are filtered directly on Unifilter GF/C glass fiber filters (soaked for 1 hour in 0.1% polyethyleneimine) under vacuum and immediately washed with 3×0.2 ml assay buffer. Non-specific uptake is determined using citalopram (10 µM final concentration). Citalopram is included as reference in all experiments as dose-response curve.

Measurements of [$^3$1H]Noradrenaline Uptake into Rat Cortical Synaptosomes

Fresh cortex from male Wistar rats (125-225 g) are homogenized in 0.4 M sucrose with a glass/teflon homogenizer. The homogenate is centrifuged at 600× g for 10 min at 4° C. The pellet is discarded and the supernatant is centrifuged at 20.000× g for 55 min. The final pellet is homogenized (20 sec) in this assay buffer (6 mg original tissue/mL=4 mg/well).

Test compounds (or buffer) and 10 nM [$^3$H]-noradrenaline are added to deep 96 well plates and shaken briefly. Composition of assay buffer: 123 mM NaCl, 4.82 mM KCl, 0.973 mM CaCl$_2$, 1.12 mM MgSO$_4$, 12.66 mM Na$_2$HPO$_4$, 2.97 mM NaH$_2$PO$_4$, 0.162 mM EDTA, 10 mM glucose and 1 mM ascorbic acid. Buffer is oxygenated with 95% O$_2$/5% CO$_2$ for 10 min at 37° C. and pH is adjusted 7.4. The incubation is started by adding tissue to a final assay volume of 1 ml. After 15 min incubation with radioligand at 37° C., samples are filtered directly on Unifilter GF/C glass fiber filters (soaked for 1 hour in 0.1% polyethyleneimine) under vacuum and immediately washed with 3×1 mL assay buffer. Non-specific uptake is determined using talsupram (10 µM final concentration). Duloxetine is included as reference in all experiments as dose-response curve.

Measurements of [$^3$H]Dopamine Uptake into Rat Cortical Synaptosomes

Tissue preparation: male wistar rats (125-250 g) are sacrificed by decapitated and striatum quickly dissected out and placed in 40 vol (w/v) ice cold 0.40 M sucrose. The tissue is gently homogenised (glass teflon homogeniser) and the P2 fraction is obtained by centrifugation (1000 g, 10 minutes and 40000 g, 20 minutes, 4° C.) and suspended in 560 volumes of a modified Krebs-Ringer-phosphate buffer, pH 7.4.

Tissue 0.25 mg/well (140 µl) (original tissue) is mixed with test suspension. After 5 minutes pre-incubation 12.5 nM 3H-dopamine is added and the mixture is incubated for 5 minutes at RT.

The incubation is terminated by filtering the samples under vacuum through Whatman GF/C filters with a wash of 1 ml buffer. The filters are dried and appropriate scintillation fluid (Optiphase Supermix) is added. After storage for 2 hours in the dark the content of radioactivity is determined by liquid scintillation counting. Uptake is obtained by subtracting the non-specific binding and passive transport measured in the presence of 100 µM of benztropine. For determination of the inhibition of uptake ten concentrations of drugs covering 6 decades are used.

$^3$H-DA=3,4-(ring-2,5,6-$^3$H)dopamine hydrochloride from New England Nuclear, specific activity 30-50 Ci/mmol.

Hyttel, Biochem. Pharmacol. 1978, 27, 1063-1068;

Hyttel, Prog. Neuro-Psychopharmacol. & bil. Psychiat. 1982, 6, 277-295;

Hyttel & Larsen, Acta Pharmacol. Tox. 1985, 56, suppl. 1, 146-153.

The invention claimed is:

1. A compound having the general formula I as the free base or salts thereof

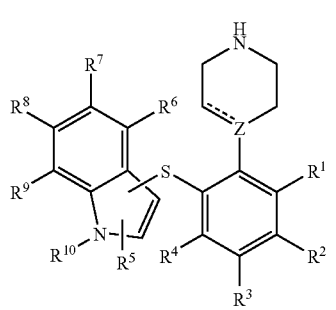

wherein
the dotted line represents an optional bond;
each of $R^1$-$R^4$ is independently selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl;
$R^5$ is selected from the group consisting of hydrogen, halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl and $C_{1-6}$-alk(en/yn)ylsulfonyl;
each of $R^6$-$R^9$ is independently selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylsulfanyl, halo-$C_{1-6}$-alk(en/yn)yl, halo-$C_{1-6}$-alk(en/yn)ylsulfonyl, halo-$C_{1-6}$-alk(en/yn)ylsulfanyl, $C_{1-6}$-alk(en/yn)ylsulfonyl and $C_{1-6}$-alk(en/yn)yl-O—CO—;
$R^{10}$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;
Z is selected from the group consisting of N, CH and C, with the proviso that the dotted line represents a bond when Z is C and the dotted line does not represent a bond when Z is CH or N.

2. A compound according to claim 1, wherein each of $R^1$-$R^4$ is independently selected from the group consisting of hydrogen, halogen and $C_{1-6}$-alk(en/yn)yl.

3. A compound according to claim 1, wherein $R^5$ is selected from the group consisting of hydrogen and $C_{1-6}$-alk(en/yn)yl.

4. A compound according to claim 1, wherein each of $R^6$-$R^9$ is independently selected from the group consisting of hydrogen, halogen, nitro, $C_{1-6}$-alk(en/yn)yl, $C_{1-6}$-alk(en/yn)yloxy and $C_{1-6}$-alk(en/yn)yl-O—CO—.

5. A compound according to claim 1, wherein $R^{10}$ is selected from the group consisting of hydrogen and $C_{1-6}$-alk(en/yn)yl.

6. A compound according to claim 1, wherein the dotted line represents a bond and Z is a carbon atom.

7. A compound according to claim 1, wherein Z is a nitrogen atom and the dotted line does not represent a line.

8. A compound according to claim 1, wherein Z represents CH and the dotted line does not represent a bond.

9. A compound selected from the group consisting of:
3-(2-piperazin-1-yl-phenylsulfanyl)-1H-indole,
4-Methoxy-3-(2-piperazin-1-yl-phenylsulfanyl)-1H-indole,
3-(2-piperazin-1-yl-phenylsulfanyl)-1H-indole-7-carboxylic acid methyl ester,
5-Nitro-3-(2-piperazin-1-yl-phenylsulfanyl)-1H-indole,
6-Chloro-3-(2-piperazin-1-yl-phenylsulfanyl)-1H-indole,
6-Methoxy-3-(2-piperazin-1-yl-phenylsulfanyl)-1H-indole,
6-Fluoro-3-(2-piperazin-1-yl-phenylsulfanyl)-1H-indole,
7-Methyl-3-(2-piperazin-1-yl-phenylsulfanyl)-1H-indole,
3-[2-(1,2,3,6-Tetrahydro-pyridin-4-yl)-phenylsulfanyl]-1H-indole,
6-Methyl-3-(2-piperazin-1-yl-phenylsulfanyl)-1H-indole,
4-Fluoro-3-(2-piperazin-1-yl-phenylsulfanyl)-1H-indole,
5-Fluoro-3-(2-piperazin-1-yl-phenylsulfanyl)-1H-indole,
4-Methyl-3-(4-methyl-2-piperazin-1-yl-phenylsulfanyl)-1H-indole,
6-Fluoro-3-(4-methyl-2-piperazin-1-yl-phenylsulfanyl)-1H-indole,
4-Fluoro-3-(4-methyl-2-piperazin-1-yl-phenylsulfanyl)-1H-indole,
7-Fluoro-3-(4-methyl-2-piperazin-1-yl-phenylsulfanyl)-1H-indole,
5-Methoxy-4-methyl-3-(4-methyl-2-piperazin-1-yl-phenylsulfanyl)-1H-indole,
5-Methoxy-3-(4-methyl-2-piperazin-1-yl-phenylsulfanyl)-1H-indole,
7-Methoxy-3-(4-methyl-2-piperazin-1-yl-phenylsulfanyl)-1H-indole,
4-Methoxy-3-(4-methyl-2-piperazin-1-yl-phenylsulfanyl)-1H-indole,
4-Chloro-3-(4-methyl-2-piperazin-1-yl-phenylsulfanyl)-1H-indole,
7-Chloro-3-(4-methyl-2-piperazin-1-yl-phenylsulfanyl)-1H-indole,
1-Methyl-3-(4-methyl-2-piperazin-1-yl-phenylsulfanyl)-1H-indole,
3-Methyl-2-(4-methyl-2-piperazin-1-yl-phenylsulfanyl)-1H-indole,
2-Methyl-3-(2-piperazin-1-yl-phenylsulfanyl)-1H-indole,
5-Methyl-3-(2-piperazin-1-yl-phenylsulfanyl)-1H-indole,
4-Methyl-3-(2-piperazin-1-yl-phenylsulfanyl)-1H-indole,
7-Fluoro-3-(2-piperazin-1-yl-phenylsulfanyl)-1H-indole,
7-Ethyl-3-(2-piperazin-1-yl-phenylsulfanyl)-1H-indole,
5-Methoxy-4-methyl-3-(2-piperazin-1-yl-phenylsulfanyl)-1H-indole,
5-Methoxy-3-(2-piperazin-1-yl-phenylsulfanyl)-1H-indole,
7-Methoxy-3-(2-piperazin-1-yl-phenylsulfanyl)-1H-indole,
5-Fluoro-2-methyl-3-(2-piperazin-1-yl-phenylsulfanyl)-1H-indole,
5-Chloro-3-(2-piperazin-1-yl-phenylsulfanyl)-1H-indole,
4-Chloro-3-(2-piperazin-1-yl-phenylsulfanyl)-1H-indole,
7-Chloro-3-(2-piperazin-1-yl-phenylsulfanyl)-1H-indole,
1-Methyl-3-(2-piperazin-1-yl-phenylsulfanyl)-1H-indole, 3-Methyl-2-(2-piperazin-1-yl-phenylsulfanyl)-1H-indole,
6-Methyl-3-(4-methyl-2-piperazin-1-yl-phenylsulfanyl)-1H-indole,
2-Methyl-3-(4-methyl-2-piperazin-1-yl-phenylsulfanyl)-1H-indole,
5-Methyl-3-(4-methyl-2-piperazin-1-yl-phenylsulfanyl)-1H-indole,
7-Methyl-3-(4-methyl-2-piperazin-1-yl-phenylsulfanyl)-1H-indole,
3-(2-Piperidin-4-yl-phenylsulfanyl)-1H-indole,
2-Methyl-3-(2-piperidin-4-yl-phenylsulfanyl)-1H-indole,
1-Methyl-3-(2-piperidin-4-yl-phenylsulfanyl)-1H-indole,
5-Methyl-3-(2-piperidin-4-yl-phenylsulfanyl)-1H-indole,
7-Fluoro-3-(2-piperidin-4-yl-phenylsulfanyl)-1H-indole,
6-Fluoro-3-(2-piperidin-4-yl-phenylsulfanyl)-1H-indole,
5-Methoxy-4-methyl-3-(2-piperidin-4-yl-phenylsulfanyl)-1H-indole,
4-Fluoro-3-(2-piperidin-4-yl-phenylsulfanyl)-1H-indole,
7-Methyl-3-(2-piperidin-4-yl-phenylsulfanyl)-1H-indole,
4-Methyl-3-(2-piperidin-4-yl-phenylsulfanyl)-1H-indole,
4-Chloro-3-(2-piperidin-4-yl-phenylsulfanyl)-1H-indole,
6-Chloro-3-(2-piperidin-4-yl-phenylsulfanyl)-1H-indole,
5-Fluoro-3-(2-piperidin-4-yl-phenylsulfanyl)-1H-indole,
5-Methoxy-3-(2-piperidin-4-yl-phenylsulfanyl)-1H-indole,
5-Chloro-3-(2-piperidin-4-yl-phenylsulfanyl)-1H-indole,
7-Methoxy-3-(2-piperidin-4-yl-phenylsulfanyl)-1H-indole,
7-Chloro-3-(2-piperidin-4-yl-phenylsulfanyl)-1H-indole,
7-Ethyl-3-(2-piperidin-4-yl-phenylsulfanyl)-1H-indole,
3-Methyl-2-(2-piperidin-4-yl-phenylsulfanyl)-1H-indole,
6-Methyl-3-(2-piperidin-4-yl-phenylsulfanyl)-1H-indole, and
5-Fluoro-2-methyl-3-(2-piperidin-4-yl-phenylsulfanyl)-1H-indole;
or a pharmaceutically acceptable salt thereof.

10. A pharmaceutical composition comprising a compound according to claim 1 or a pharmaceutically acceptable salt thereof, and at least one pharmaceutically acceptable carrier or diluent.

11. A method for treatment of an affective disorder, comprising administering to a subject in need thereof a therapeutically effective amount of a compound according to claim 1 or a pharmaceutically acceptable salt thereof.

12. The method according to claim 11, wherein the affective disorder is a depressive disorder.

13. The method according to claim 11, wherein the affective disorder is an anxiety disorder.

14. A method for treatment of a pain disorder, comprising administering to a subject in need thereof a therapeutically effective amount of a compound according to claim 1 or a pharmaceutically acceptable salt thereof.

15. The method according to claim 14, wherein the pain disorder is selected from the group consisting of fibromyalgia syndrome, overall pain, back pain, shoulder pain, headache, pain while awake, and pain during daily activities.

16. A method for treatment of attention deficit hyperactivity disorder, comprising administering to a subject in need thereof a therapeutically effective amount of a compound according to claim 1 or a pharmaceutically acceptable salt thereof.

17. A method for treatment of stress urinary incontinence, comprising administering to a subject in need thereof a therapeutically effective amount of a compound according to claim 1 or a pharmaceutically acceptable salt thereof.

18. The method according to claim 12, wherein the depressive disorder is selected from the group consisting of major depressive disorder, postnatal depression, dysthymia, depression associated with bipolar disorder, depression associated with Alzheimer's, depression associated with psychosis and depression associated with Parkinson's.

19. The method according to claim 13, wherein the anxiety disorder is selected from the group consisting of general anxiety disorder, social anxiety disorder, post traumatic stress disorder, obsessive compulsive disorder, panic disorder, panic attacks, specific phobias, social phobia and agoraphobia.

20. A pharmaceutical composition comprising a compound according to claim 9 or a pharmaceutically acceptable salt thereof and at least one pharmaceutically acceptable carrier or diluent.

21. A method for treatment of an affective disorder, comprising administering to a subject in need thereof a therapeutically effective amount of a compound according to claim 9 or a pharmaceutically acceptable salt thereof.

22. The method according to claim 21, wherein the affective disorder is a depressive disorder.

23. The method according to claim 22, wherein the depressive disorder is selected from the group consisting of major depressive disorder, postnatal depression, dysthymia, depression associated with bipolar disorder, depression associated with Alzheimer's, depression associated with psychosis and depression associated with Parkinson's.

24. The method according to claim 21, wherein the affective disorder is an anxiety disorder.

25. The method according to claim 24, wherein the anxiety disorder is selected from the group consisting of general anxiety disorder, social anxiety disorder, post traumatic stress disorder, obsessive compulsive disorder, panic disorder, panic attacks, specific phobias, social phobia and agoraphobia.

26. A method for treatment of a pain disorder, comprising administering to a subject in need thereof a therapeutically effective amount of a compound according to claim 9 or a pharmaceutically acceptable salt thereof.

27. The method according to claim 26, wherein the pain disorder is selected from the group consisting of fibromyalgia syndrome, overall pain, back pain, shoulder pain, headache, pain while awake and pain during daily activities.

28. A method for treatment of attention deficit hyperactivity disorder, comprising administering to a subject in need thereof a therapeutically effective amount of a compound according to claim 9 or a pharmaceutically acceptable salt thereof.

29. A method for treatment of stress urinary incontinence, comprising administering to a subject in need thereof a therapeutically effective amount of a compound according to claim 9 or a pharmaceutically acceptable salt thereof.

* * * * *

UNITED STATES PATENT AND TRADEMARK OFFICE
CERTIFICATE OF CORRECTION

PATENT NO. : 7,678,800 B2  Page 1 of 1
APPLICATION NO. : 11/629043
DATED : March 16, 2010
INVENTOR(S) : Jan Kehler et al.

It is certified that error appears in the above-identified patent and that said Letters Patent is hereby corrected as shown below:

On Title page 1, column 1, lines 7-9, "(75) Inventors: Jan Kehler, Lyngby (DK); Friedrich Kroll, Mechelen (BE); Karsten Juhl, Greve (DK)" should read --(75) Inventors: Jan Kehler, Kgs. Lyngby (DK); Friedrich Kroll, Mechelen (BE); Karsten Juhl, Greve (DK)--.

Signed and Sealed this

Eleventh Day of May, 2010

David J. Kappos
*Director of the United States Patent and Trademark Office*